(12) United States Patent
Sasano et al.

(10) Patent No.: US 11,396,666 B2
(45) Date of Patent: Jul. 26, 2022

(54) METHOD FOR PRODUCING (1R,3R)-3-(TRIFLUOROMETHYL) CYCLOHEXAN-1-OL AND INTERMEDIATE THEREOF

(71) Applicant: API CORPORATION, Tokyo (JP)

(72) Inventors: Haruka Sasano, Tokyo (JP); Takanobu Iura, Tokyo (JP); Kenji Oki, Tokyo (JP)

(73) Assignee: API CORPORATION, Tokyo (JP)

( * ) Notice: Subject to any disclaimer, the term of this patent is extended or adjusted under 35 U.S.C. 154(b) by 0 days.

(21) Appl. No.: 17/284,912

(22) PCT Filed: Apr. 17, 2020

(86) PCT No.: PCT/JP2020/016948
§ 371 (c)(1),
(2) Date: Apr. 13, 2021

(87) PCT Pub. No.: WO2020/213731
PCT Pub. Date: Oct. 22, 2020

(65) Prior Publication Data
US 2022/0098623 A1 Mar. 31, 2022

Related U.S. Application Data

(60) Provisional application No. 62/836,324, filed on Apr. 19, 2019.

(51) Int. Cl.
| | | |
|---|---|---|
| C12P 7/02 | (2006.01) |
| C12P 7/04 | (2006.01) |
| C12N 9/16 | (2006.01) |
| C12P 7/26 | (2006.01) |
| C12N 9/02 | (2006.01) |

(52) U.S. Cl.
CPC .............. *C12P 7/02* (2013.01); *C12P 7/26* (2013.01); *C12N 9/0004* (2013.01); *C12N 9/16* (2013.01); *C12Y 401/02* (2013.01)

(58) Field of Classification Search
CPC .............. C12N 9/0004; C12N 9/0008; C12N 2800/80; C12Y 401/02; C12P 7/02
USPC .......... 435/155, 189, 192, 320.1, 252.3, 157
See application file for complete search history.

(56) References Cited

U.S. PATENT DOCUMENTS

| | | |
|---|---|---|
| 2006/0035357 A1 | 2/2006 | Kizaki et al. |
| 2009/0093031 A1 | 4/2009 | Liang et al. |
| 2013/0078692 A1 | 3/2013 | Liang et al. |
| 2020/0080064 A1 | 3/2020 | Yakunin et al. |

FOREIGN PATENT DOCUMENTS

| | | |
|---|---|---|
| CN | 101784669 A | 7/2010 |
| CN | 101855342 A | 10/2010 |
| CN | 107849521 A | 3/2018 |
| WO | WO 2004/027055 A1 | 4/2004 |
| WO | WO 2008/042876 A2 | 4/2008 |
| WO | WO 2011/052718 A1 | 5/2011 |

OTHER PUBLICATIONS

Witkowski et al., Biochemistry 38:11643-11650, 1999.*
Whisstock et al., Quarterly Reviews of Biophysics 2003, vol. 36 (3): 307-340.*
Devos et al., Proteins: Structure, Function and Genetics, 2000, vol. 41: 98-107.*
ISR for PCT/JP2020/016948, dated Jul. 14, 2020 (w/ translation).
Written Opinion of the International Searching Authority for PCT/JP2020/016948, dated Jul. 14, 2020 (w/ translation).
Fitzpatrick et al., "Characterization of YqjM, an Old Yellow Enzyme Homolog from *Bacillus subtilis* Involved in the Oxidative Stress Response", Journal of Biological Chemistry, 278(22):19891-19897, 2003.
Bradshaw et al., "Lactobacillys kefir alcohol dehydrogenase: a useful catalyst for synthesis", J. Org. Chem., 57(5):1532-1536, 1992.
Bougioukou et al., "Directed Evolution of an Enantioselective Enoate-Reductase: Testing the Utility of Interative Saturation Mutagenesis", Adv. Synth. Catal., 351:3287-3305, 2009.

(Continued)

*Primary Examiner* — Robert B Mondesi
*Assistant Examiner* — Mohammad Y Meah
(74) *Attorney, Agent, or Firm* — Greenblum & Bernstein, P.L.C.

(57) ABSTRACT

A method for producing a compound represented by formula (3) including bringing a carbon-carbon double bond reductase, a microorganism or cell having an ability to produce the enzyme, a processed product of the microorganism or cell, and/or a culture solution containing the enzyme which is obtained by culturing the microorganism or cell, and a carbonyl reductase, a microorganism or cell having an ability to produce the enzyme, a processed product of the microorganism or cell, and/or a culture solution containing the enzyme which is obtained by culturing the microorganism or cell into contact with a compound represented by formula (1) to obtain a compound represented by formula (3):

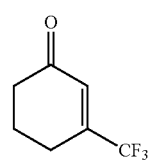

(1)

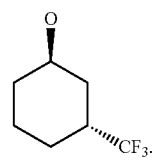

(3)

8 Claims, No Drawings

Specification includes a Sequence Listing.

(56) References Cited

OTHER PUBLICATIONS

Arnone et al., "Trifluoromethyl vs. methyl ability to direct enantioselection in microbial reduction of carbonyl substrates", Tetrahedron, 54(12): 2809-2818, 1998.
Office Action for CN App. No. 202080028670.8, dated Jan. 17, 2022 (w/ translation).

* cited by examiner

SEQUENCE LISTING

<160> NUMBER OF SEQ ID NOS: 10

<210> SEQ ID NO 1
<211> LENGTH: 338
<212> TYPE: PRT
<213> ORGANISM: Bacillus subtilis

<400> SEQUENCE: 1

Met Ala Arg Lys Leu Phe Thr Pro Ile Thr Ile Lys Asp Met Thr Leu
1               5                   10                  15

Lys Asn Arg Ile Val Met Ser Pro Met Cys Met Tyr Ser Ser His Glu
            20                  25                  30

Lys Asp Gly Lys Leu Thr Pro Phe His Met Ala His Tyr Ile Ser Arg
            35                  40                  45

Ala Ile Gly Gln Val Gly Leu Ile Ile Val Glu Ala Ser Ala Val Asn
 50                  55                  60

Pro Gln Gly Arg Ile Thr Asp Gln Asp Leu Gly Ile Trp Ser Asp Glu
 65                  70                  75                  80

His Ile Glu Gly Phe Ala Lys Leu Thr Glu Gln Val Lys Glu Gln Gly
                 85                  90                  95

Ser Lys Ile Gly Ile Gln Leu Ala His Ala Gly Arg Lys Ala Glu Leu
            100                 105                 110

Glu Gly Asp Ile Phe Ala Pro Ser Ala Ile Ala Phe Asp Gly Gln Ser
            115                 120                 125

Ala Thr Pro Val Glu Met Ser Ala Glu Lys Val Lys Glu Thr Val Gln
130                 135                 140

Glu Phe Lys Gln Ala Ala Ala Arg Ala Lys Glu Ala Gly Phe Asp Val
145                 150                 155                 160

Ile Glu Ile His Ala Ala His Gly Tyr Leu Ile His Glu Phe Leu Ser
                165                 170                 175

Pro Leu Ser Asn His Arg Thr Asp Glu Tyr Gly Gly Ser Pro Glu Asn
            180                 185                 190

Arg Tyr Arg Phe Leu Arg Glu Ile Ile Asp Glu Val Lys Gln Val Trp
            195                 200                 205

Asp Gly Pro Leu Phe Val Arg Val Ser Ala Ser Asp Tyr Thr Asp Lys
            210                 215                 220

Gly Leu Asp Ile Ala Asp His Ile Gly Phe Ala Lys Trp Met Lys Glu
225                 230                 235                 240

Gln Gly Val Asp Leu Ile Asp Cys Ser Ser Gly Ala Leu Val His Ala
                245                 250                 255

Asp Ile Asn Val Phe Pro Gly Tyr Gln Val Ser Phe Ala Glu Lys Ile
            260                 265                 270

Arg Glu Gln Ala Asp Met Ala Thr Gly Ala Val Gly Met Ile Thr Asp
            275                 280                 285

Gly Ser Met Ala Glu Glu Ile Leu Gln Asn Gly Arg Ala Asp Leu Ile
290                 295                 300

Phe Ile Gly Arg Glu Leu Leu Arg Asp Pro Phe Phe Ala Arg Thr Ala
305                 310                 315                 320

Ala Lys Gln Leu Asn Thr Glu Ile Pro Ala Pro Val Gln Tyr Glu Arg
                325                 330                 335

Gly Trp

<210> SEQ ID NO 2
<211> LENGTH: 252
<212> TYPE: PRT
<213> ORGANISM: Lactobacillus kefir

<400> SEQUENCE: 2

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
            35                  40                  45

Lys Ser Ile Gly Gly Thr Asp Val Ile Arg Phe Val Gln His Asp Ala
 50                  55                  60

```
Ser Asp Glu Ala Gly Trp Thr Lys Leu Phe Asp Thr Thr Glu Glu Ala
 65                  70                  75                  80

Phe Gly Pro Val Thr Thr Val Val Asn Asn Ala Gly Ile Ala Val Ser
                 85                  90                  95

Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Ile
130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Met Met Ser Gln
            195                 200                 205

Arg Thr Lys Thr Pro Met Gly His Ile Gly Glu Pro Asn Asp Ile Ala
210                 215                 220

Trp Ile Cys Val Tyr Leu Ala Ser Asp Glu Ser Lys Phe Ala Thr Gly
225                 230                 235                 240

Ala Glu Phe Val Val Asp Gly Tyr Thr Ala Gln
                245                 250

<210> SEQ ID NO 3
<211> LENGTH: 234
<212> TYPE: PRT
<213> ORGANISM: Pichia finlandica

<400> SEQUENCE: 3

Leu Ser Val Ala Lys Lys Phe Leu Gln Leu Gly Ala Lys Val Thr Ile
1               5                  10                   15

Ser Asp Val Ser Gly Glu Lys Lys Tyr His Glu Thr Val Val Ala Leu
                20                  25                   30

Lys Ala Gln Asn Leu Asn Thr Asp Asn Leu His Tyr Val Gln Ala Asp
            35                  40                  45

Ser Ser Lys Glu Glu Asp Asn Lys Lys Leu Ile Ser Glu Thr Leu Ala
        50                  55                  60

Thr Phe Gly Gly Leu Asp Ile Val Cys Ala Asn Ala Gly Ile Gly Lys
65                  70                  75                  80

Phe Ala Pro Thr His Glu Thr Pro Phe Asp Val Trp Lys Lys Val Ile
                85                  90                  95

Ala Val Asn Leu Asn Gly Val Phe Leu Leu Asp Lys Leu Ala Ile Asn
            100                 105                 110

Tyr Trp Leu Glu Lys Ser Lys Pro Gly Val Ile Val Asn Met Gly Ser
            115                 120                 125

Val His Ser Phe Val Ala Ala Pro Gly Leu Ala His Tyr Gly Ala Ala
130                 135                 140

Lys Gly Gly Val Lys Leu Leu Thr Gln Thr Leu Ala Leu Glu Tyr Ala
145                 150                 155                 160

Ser His Gly Ile Arg Val Asn Ser Val Asn Pro Gly Tyr Ile Ser Thr
                165                 170                 175

Pro Leu Ile Asp Glu Val Pro Lys Glu Arg Leu Asp Lys Leu Val Ser
            180                 185                 190
```

Leu His Pro Ile Gly Arg Leu Gly Arg Pro Glu Glu Val Ala Asp Ala
        195                 200                 205

Val Ala Phe Leu Cys Ser Gln Glu Ala Thr Phe Ile Asn Gly Val Ser
210                 215                 220

Leu Pro Val Asp Gly Gly Tyr Thr Ala Gln
225                 230

<210> SEQ ID NO 4
<211> LENGTH: 210
<212> TYPE: PRT
<213> ORGANISM: Devosia riboflavina

<400> SEQUENCE: 4

Leu Glu Gly Ala Gln Ala Val Ala Asp Ala Val Lys Ala Ala Gly Gly
1               5                   10                  15

Glu Ala Ala Ala Val Ala Val Asp Val Ala Lys Ala Asp Gln Val Glu
            20                  25                  30

Lys Ala Val Gln Phe Ala Val Asp Thr Phe Gly Ala Leu His Leu Ala
        35                  40                  45

Val Asn Asn Ala Gly Ile Gly Gly Ala Ser Ala Pro Leu Gly Asp Tyr
    50                  55                  60

Ser Phe Asp Asp Trp His Arg Val Ile Asp Val Asn Leu Asn Ser Val
65                  70                  75                  80

Phe Tyr Ser Met Lys Tyr Glu Ile Val Ala Met Leu Arg Ala Gly Gly
                85                  90                  95

Gly Ala Ile Val Asn Met Ala Ser Ile Leu Gly Ser Val Thr Phe Pro
            100                 105                 110

Asn Ala Pro Ala Tyr Val Thr Ala Lys His Gly Val Val Gly Met Thr
        115                 120                 125

Lys Ser Ala Ala Val Asp Tyr Ala Lys Lys Gly Ile Arg Val Thr Ala
    130                 135                 140

Val Gly Pro Gly Phe Ile Asp Thr Pro Leu Leu Ser Ala Leu Pro Lys
145                 150                 155                 160

Glu Thr Leu Asp Tyr Leu Lys Ser Val His Pro Ile Gly Arg Leu Gly
                165                 170                 175

Thr Ser Asp Glu Val Ala Ala Leu Thr Ala Phe Leu Leu Ser Asp Ala
            180                 185                 190

Ala Ser Asn Ile Thr Gly Ser Tyr His Leu Val Asp Gly Gly Tyr Val
        195                 200                 205

Ala Gln
    210

<210> SEQ ID NO 5
<211> LENGTH: 1017
<212> TYPE: DNA
<213> ORGANISM: Bacillus subtilis

<400> SEQUENCE: 5
atggccagaa aattatttac acctattaca attaaagata tgacgttaaa aaaccgcatt      60
gtcatgtcgc caatgtgcat gtattcttct catgaaaagg acggaaaatt aacaccgttc     120
cacatggcac attacatatc gcgcgcaatc ggccaggtcg gactgattat tgtagaggcg     180
tcagcggtta accctcaagg acgaatcact gaccaagact taggcatttg gagcgacgag     240
catattgaag gctttgcaaa actgactgag caggtcaaag aacaaggttc aaaaatcggc     300
attcagcttg cccatgccgg acgtaaagct gagcttgaag gagatatctt cgctccatcg     360

```
gcgattgcgt tgacgaaca atcagcaaca cctgtagaaa tgtcagcaga aaaagtaaaa    420
gaaacggtcc aggagttcaa gcaagcggct gcccgcgcaa aagaagccgg ctttgatgtg    480
attgaaattc atgcggcgca cggatattta attcatgaat ttttgtctcc gctttccaac    540
catcgaacag atgaatatgg cggctcacct gaaaaccgct atcgtttctt gagagagatc    600
attgatgaag tcaaacaagt atgggacggt cctttatttg tccgtgtatc tgcttctgac    660
tacactgata aaggcttaga cattgccgat cacatcggtt tgcaaaatg gatgaaggag    720 cagggtgttg acttaattga ctgcagctca ggcgcccttg ttcacgcaga cattaacgta    780
ttccctggct atcaggtcag cttcgctgag aaaatccgtg aacaggcgga catggctact    840
ggtgccgtcg gcatgattac agacggttca atggctgaag aaattctgca aaacggacgt    900
gccgacctca tctttatcgg cagagagctt ttgcgggatc catttttttgc aagaactgct    960 gcgaaacagc tcaatacaga gattccggcc cctgttcaat acgaaagagg ctggtaa     1017

<210> SEQ ID NO 6
<211> LENGTH: 759
<212> TYPE: DNA
<213> ORGANISM: Lactobacillus kefir

<400> SEQUENCE: 6
atgactgatc gtttaaaagg caaagtagca attgtaactg gcggtacctt gggaattggc     60
ttggcaatcg ctgataagtt tgttgaagaa ggcgcaaagg ttgttattac cggccgtcac    120
gctgatgtag gtgaaaaagc tgccaaatca atcggcggca cagacgttat ccgttttgtc    180
caacacgatg cttctgatga agccggctgg actaagttgt tgatacgac tgaagaagca    240 tttggcccag ttaccacggt tgtcaacaat gccggaattg cggtcagcaa gagtgttgaa    300
gataccacaa ctgaagaatg gcgcaagctg ctctcagtta acttggatgg tgtcttcttc    360
ggtacccgtc ttggaatcca acgtatgaag aataaaggac tcggagcatc aatcatcaat    420
atgtcatcta tcgaaggttt tgttggtgat ccaactctgg gtgcatacaa cgcttcaaaa    480
ggtgctgtca gaattatgtc taaatcagct gccttggatt gcgctttgaa ggactacgat    540
gttcgggtta acactgttca tccaggttat atcaagacac cattggttga cgatcttgaa    600
ggggcagaag aaatgatgtc acagcggacc aagacaccaa tgggtcatat cggtgaacct    660
aacgatatcg cttggatctg tgtttacctg gcatctgacg aatctaaatt tgccactggt    720
gcagaattcg ttgtcgatgg tggatacact gctcaataa                           759

<210> SEQ ID NO 7
<211> LENGTH: 765
<212> TYPE: DNA
<213> ORGANISM: Pichia finlandica

<400> SEQUENCE: 7
atgtcttata acttccataa caaggttgca gttgttactg gagctctatc aggaatcggc     60
ttaagcgtcg caaaaaagtt ccttcagctc ggcgccaaag taacgatctc tgatgtcagt    120
ggagagaaaa aatatcacga gactgttgtt gctctgaaag cccaaaatct caacactgac    180
aacctccatt atgtacaggc agattccagc aaagaagaag ataacaagaa attgatttcg    240
gaaactctgg caacctttgg gggcctggat attgtttgtg ctaatgcagg aattggaaag    300
ttcgctccca cccatgaaac acccttcgac gtatggaaga aggtgattgc tgtgaatttg    360
aatggagtat tcttactgga taagctagcc atcaattact ggctagagaa aagcaaaccc    420
```

-continued

```
ggcgtaattg tcaacatggg atcagtccac tcttttgtag cagctcctgg ccttgcgcat    480
tatggagctg caaaaggcgg tgtcaaactg ttaacacaaa cattggctct agagtacgca    540
tctcatggta ttagagtaaa ttctgtcaat ccggggtaca tttcgactcc tttgatagat    600
gaggttccga agagcggtt ggataaactt gtaagcttgc accctattgg agactaggt      660 cgtccagagg aagttgctga tgcagtcgca tttctgtgtt cccaggaggc cactttcatc    720
aacggcgttt ctttgccggt tgacgggggg tacacagccc agtaa                    765
```

<210> SEQ ID NO 8
<211> LENGTH: 753
<212> TYPE: DNA
<213> ORGANISM: Devosia riboflavina

<400> SEQUENCE: 8

```
atgtcccagg atttttcagg caaggtcgca ttcgtaacgg tggtgcctc gggcatcggt     60 gaggcggtcg tcaagcagct tgccgcgcgc ggcgccaagg ttgtggttgc cgatctcaag    120
ctcgaaggcg cgcaggcggt tgccgatgcg gtcaaggccc ccggcggcga agcggccgcg    180
gtagctgtcg atgtcgccaa ggccgatcag gtggagaagg ctgtccagtt cgccgtcgac    240
acctttggcg ccctgcatct ggcggtcaat aatgccggca ttggcggcgc ttccgctccc    300
ctcggcgatt attccttcga cgactggcat agggttatcg acgtcaatct caattccgtc    360
ttctattcga tgaagtacga gatcgtcgcc atgctcaggg caggcggtgg cgccatcgtc    420
aacatggcct ccatcctcgg ctcggtgacc tttcccaatg caccggccta tgtcaccgcc    480
aagcacggcg tggtcggcat gaccaagtcg gccgcggtgg actatgccaa aaagggcatt    540
cgcgtcacgg ccgtcgggcc cggtttcatc gacacgccgc tcctatccgc cttgccaag    600 gaaaccctgg actacctcaa atccgtccat ccgatcggac ggctgggtac ctcggatgaa    660
gtcgcagcgc tgaccgcgtt cctgctctcc gatgcagcgt cgaacatcac cggctcctat    720
cacctggtcg atggcggcta cgtcgcccaa tag                                 753
```

<210> SEQ ID NO 9
<211> LENGTH: 261
<212> TYPE: PRT
<213> ORGANISM: Bacillus subtilis

<400> SEQUENCE: 9

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Ala
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
```

```
                     130                 135                 140
Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
                180                 185                 190

Thr Pro Ile Asn Ala Glu Lys Phe Ala Asp Pro Lys Gln Lys Ala Asp
                195                 200                 205

Val Glu Ser Met Ile Pro Met Gly Tyr Ile Gly Glu Pro Glu Glu Ile
                210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
                260

<210> SEQ ID NO 10
<211> LENGTH: 786
<212> TYPE: DNA
<213> ORGANISM: Bacillus subtilis

<400> SEQUENCE: 10
atgtatccgg atttaaaagg aaaagtcgtc gctattacag gagctgcttc agggctcgga        60
aaggcgatgg ccattcgctt cggcaaggag caggcaaaag tggttatcaa ctattatagt       120
aataaacaag atccgaacga ggtaaaagaa gaggtcatca aggcgggcgg tgaagctgtt       180
gtcgtccaag gagatgtcac gaaagaggaa gatgtaaaaa atatcgtgca aacggcaatt       240
aaggagttcg gcacactcga tattatgatt aataatgccg gtcttgcaaa tcctgtgcca       300
tctcacgaaa tgccgctcaa ggattgggat aaagtcatcg cacgaacttt aacgggtgcc       360 ttttaggaa gccgtgaagc gattaaatat ttcgtagaaa acgatatcaa gggaaatgtc       420
attaacatgt ccagtgtgca cgaagtgatt ccttggccgt tatttgtcca ctatgcggca       480
agtaaaggcg ggataaagct gatgacagaa acattagcgt tggaatacgc gccgaagggc       540
attcgcgtca ataatattgg gccaggtgcg atcaacacgc caatcaatgc tgaaaaattc       600
gctgacccta aacagaaagc tgatgtagaa agcatgattc caatgggata tatcggcgaa       660
ccggaggaga tcgccgcagt agcagcctgg cttgcttcga aggaagccag ctacgtcaca       720
ggcatcacgt tattcgcgga cggcggtatg acactgtatc cttcattcca ggcaggccgc       780
ggttaa                                                                 786
```

METHOD FOR PRODUCING (1R,3R)-3-(TRIFLUOROMETHYL) CYCLOHEXAN-1-OL AND INTERMEDIATE THEREOF

TECHNICAL FIELD

The present invention relates to methods for producing a cyclohexane derivative, (1R,3R)-3-(trifluoromethyl)cyclohexan-1-ol, and intermediates thereof, which are useful as starting materials and intermediates for synthesizing pharmaceutical products.

BACKGROUND ART (1R,3R)-3-(trifluoromethyl)cyclohexan-1-ol, intermediates thereof and derivatives thereof are useful as starting materials and intermediates for synthesizing various pharmaceutical products.

As a production method of (1R,3R)-3-(trifluoromethyl) cyclohexan-1-ol, a biological method for producing same from a racemate, 3-trifluoromethylcyclohexanone, has been known (non-patent document 4).

However, the reaction did not proceed sufficiently with the microorganism used in non-patent document 4, the yield was as low as about 34%, and the optical purity of the obtained (1R,3R)-3-(trifluoromethyl)cyclohexan-1-ol was also as low as about 39% compared to 4 kinds of isomers, thus demonstrating low optical selectivity (Run14). Consequently, it is difficult to produce the desired product with high efficiency because enantiomer (1S,3S)-3-(trifluoromethyl)cyclohexan-1-ol, and two kinds of diastereomers of (1R,3S)-3-(trifluoromethyl)cyclohexan-1-ol and (1S,3R)-3-(trifluoromethyl)cyclohexan-1-ol as by-products are produced in large amounts besides the desired (1R,3R)-3-(trifluoromethyl)cyclohexan-1-ol. Also, in the case of industrial production, a large separation device and a large purification device are required, which increases the cost and the method is not suitable as an industrial production method for an intermediate of a pharmaceutical product.

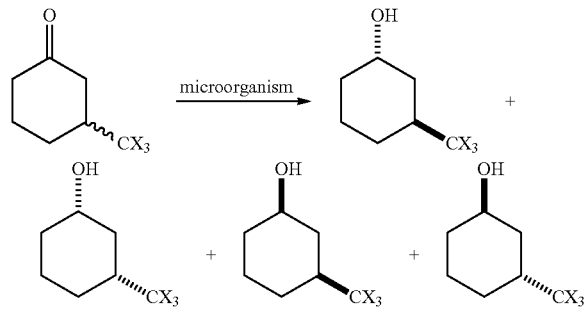

While patent documents 1, 2 and non-patent document 3 describe an enzyme that converts a carbonyl group to a hydroxyl group, they do not describe application of the enzyme to the compound of the present invention.

While patent document 3 and non-patent document 1 describe carbon-carbon double bond reductase, they do not describe application of the reductase to the compound of the present invention.

Non-patent document 2 describes a method for obtaining a compound analogous to (3R)-3-(trifluoromethyl)cyclohexan-1-one (hereinafter sometimes to be referred to as compound (2)), the method including contacting a carbonyl group and a compound analogous to 3-trifluoromethyl-2-cyclohexen-1-one (hereinafter sometimes to be referred to as compound (1)), in which the 3-position trifluoromethyl group has been replaced with a methyl group, with a specific carbon-carbon double bond reductase. However, application of a specific enzyme to the compound of the present invention is not described. As is clear from the below-mentioned Comparative Examples 1, 2 and 6, when the enzymes (YqjM variants 1, 2 and 15) described in non-patent document 2 and superior to the compound analogous to compound (1) in the reactivity and optical selectivity were contacted with compound (1), the reaction hardly proceeded.

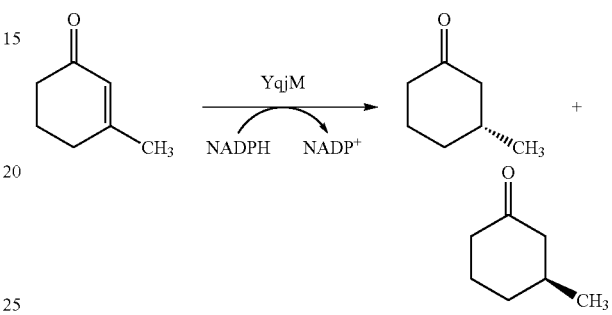

Therefore, a method for industrially producing (1R,3R)-3-(trifluoromethyl)cyclohexan-1-ol (hereinafter sometimes to be referred to as compound (3)), which is useful as an intermediate for pharmaceutical products, with high purity and high efficiency at a low cost is desired.

DOCUMENT LIST

Patent Documents patent document 1: WO 2008/042876
patent document 2: WO 2004/027055
patent document 3: WO 2011/052718

Non-Patent Documents non-patent document 1: Journal of Biological Chemistry, Vol. 278, No. 22, Issue of May 30, pp 19891-19897
non-patent document 2: Adv. Synth. Catal. 2009, 351, pp 3287-3305
non-patent document 3: J. Org. Chem., 1992, 57(5), pp 1532-1536
non-patent document 4: Tetrahedron (1998), 54(12), pp 809-2818

SUMMARY OF INVENTION

Technical Problem

The present invention aims to provide a novel method for industrially producing (1R,3R)-3-(trifluoromethyl)cyclohexan-1-ol and an intermediate thereof with high optical purity, high selectivity, and high efficiency at a low cost.

Solution to Problem

The present inventors have conducted intensive studies in an attempt to solve the above-mentioned problem and found that a carbon-carbon double bond reductase (hereinafter sometimes to be referred to as C=O reductase) derived from *Bacillus subtilis* reduces 3-trifluoromethyl-2-cyclohexen-1-one with high selectivity, and can afford (3R)-3-(trifluoromethyl)cyclohexan-1-one, which is an intermediate, with high efficiency.

In addition, they have found that a carbonyl reductase (hereinafter sometimes to be referred to as C=O reductase) derived from *Lactobacillus* kefir, *Pichia finlandica*, and *Devosia riboflavina* reduces 3-trifluoromethyl-2-cyclohexen-1-one with high selectivity, and can afford (1R)-3-trifluoromethyl-2-cyclohexen-1-ol (hereinafter sometimes to be referred to as compound (4)), which is an intermediate, with high efficiency.

Furthermore, they have found that (1R,3R)-3-(trifluoromethyl)cyclohexan-1-ol with high optical purity and high concentration can be obtained at a low cost by bringing the enzyme, a microorganism or cell having an ability to produce the enzyme, a processed product of the microorganism or cell, and/or a culture solution containing the enzyme which is obtained by culturing the microorganism or cell (hereinafter these are sometimes to be collectively referred to as "enzyme and the like") into contact with 3-trifluoromethyl-2-cyclohexen-1-one, (3R)-3-(trifluoromethyl)cyclohexan-1-one, or (1R)-3-trifluoromethyl-2-cyclohexen-1-ol. The present invention has been made based on these findings.

That is, the gist of the present invention is as follows.

[1] A method for producing a compound represented by the formula (3)

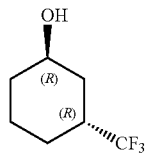
(3)

((1R,3R)-3-(trifluoromethyl)cyclohexan-1-ol (hereinafter sometimes to be referred to as compound (3))), comprising bringing a carbon-carbon double bond reductase, a microorganism or cell having an ability to produce the enzyme, a processed product of the microorganism or cell, and/or a culture solution containing the enzyme which is obtained by culturing the microorganism or cell, and a carbonyl reductase, a microorganism or cell having an ability to produce the enzyme, a processed product of the microorganism or cell, and/or a culture solution containing the enzyme which is obtained by culturing the microorganism or cell into contact with a compound represented by the formula (1)

(1)

(3-trifluoromethyl-2-cyclohexen-1-one (hereinafter sometimes to be referred to as compound (1))) to obtain the compound represented by the formula (3).

[2] The production method of the above-mentioned [1], wherein the aforementioned carbon-carbon double bond reductase comprises a protein shown in the following (A), (B) or (C):

(A) a protein having the amino acid sequence shown in SEQ ID NO: 1

(B) a protein having an amino acid sequence resulting from deletion, substitution, insertion and/or addition of 1 to plural amino acids in the amino acid sequence shown in SEQ ID NO: 1, and having an activity to catalyze reaction(s) shown in the formula (I) and/or the formula (II):

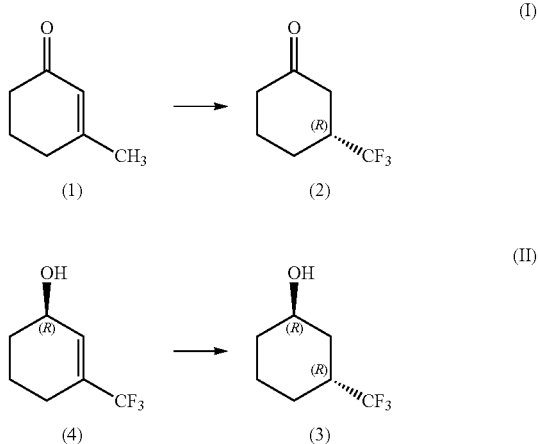

(C) a protein having an amino acid sequence with not less than 80% identity with the amino acid sequence shown in SEQ ID NO: 1, having at least one amino acid substitution selected from the following groups (i)-(ii) introduced thereinto, and having an activity to catalyze reaction(s) shown in the formula (I) and/or the formula (II)

(i) substitution of the 26th cysteine in the amino acid sequence shown in SEQ ID NO: 1 with an amino acid other than aspartic acid, phenylalanine, tryptophan and tyrosine (ii) substitution of the 104th alanine in the amino acid sequence shown in SEQ ID NO: 1 with an amino acid other than alanine

[3] The production method of the above-mentioned [2], wherein the amino acid substitution in the aforementioned (i) is the following (i'):

(i') substitution of the 26th cysteine in the amino acid sequence shown in SEQ ID NO: 1 with alanine.

[4] The production method of the above-mentioned [2] or [3], wherein the amino acid substitution in the aforementioned (ii) is the following (ii'):

(ii') substitution of the 104th alanine in the amino acid sequence shown in SEQ ID NO: 1 with histidine, phenylalanine, tryptophan or tyrosine.

[5] The production method of the above-mentioned [1] or [2], wherein the aforementioned carbonyl reductase comprises a protein shown in the following (A), (B) or (C):

(A) a protein having the amino acid sequence shown in SEQ ID NO: 2, 3 or 4

(B) a protein having an amino acid sequence resulting from deletion, substitution, insertion and/or addition of 1 to plural amino acids in the amino acid sequence shown in SEQ ID NO: 2, 3 or 4, and having an activity to catalyze reaction(s) shown in the formula (III) and/or the formula (IV):

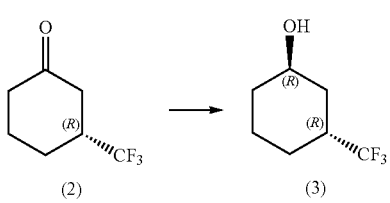

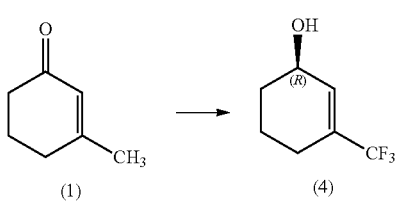

(C) a protein having an amino acid sequence with not less than 80% identity with the amino acid sequence shown in SEQ ID NO: 2, 3 or 4, and having an activity to catalyze reaction(s) shown in the formula (III) and/or the formula (IV).

[6] The production method of any of the above-mentioned [1] to [5], wherein the carbon-carbon double bond reductase, the microorganism or cell having an ability to produce the enzyme, the processed product of the microorganism or cell, and/or the culture solution containing the enzyme which is obtained by culturing the microorganism or cell is brought into contact with the compound represented by the formula (1)

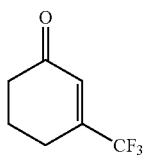

to obtain a compound represented by the formula (2)

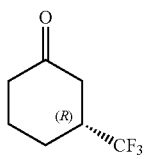

((3R)-3-(trifluoromethyl)cyclohexan-1-one (hereinafter sometimes to be referred to as compound (2))), and further the carbonyl reductase, the microorganism or cell having an ability to produce the enzyme, the processed product of the microorganism or cell, and/or the culture solution containing the enzyme which is obtained by culturing the microorganism or cell is brought into contact with the compound represented by the formula (2) to obtain the compound represented by the formula (3)

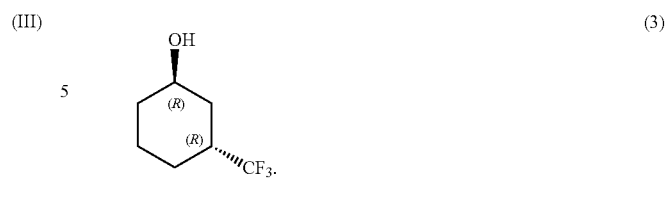

[7] The production method of any of the above-mentioned [1] to [5], wherein the carbonyl reductase, a microorganism or cell having an ability to produce the enzyme, a processed product of the microorganism or cell, and/or a culture solution containing the enzyme which is obtained by culturing the microorganism or cell is brought into contact with the compound represented by the formula (1)

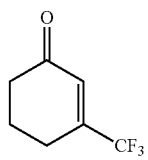

to obtain a compound represented by the formula (4)

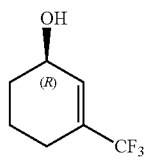

((1R)-3-trifluoromethyl-2-cyclohexen-1-ol (hereinafter sometimes to be referred to as compound (4))), and further carbon-carbon double bond reductase, a microorganism or cell having an ability to produce the enzyme, a processed product of the microorganism or cell, and/or a culture solution containing the enzyme which is obtained by culturing the microorganism or cell is brought into contact with the compound represented by the formula (4) to obtain the compound represented by the formula (3)

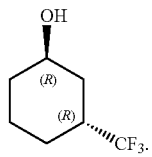

[8] The production method of any of the above-mentioned [1] to [7], wherein a content of a compound represented by the formula (5)

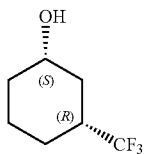

(hereinafter sometimes to be referred to as compound (5)) and/or a compound represented by the formula (6)

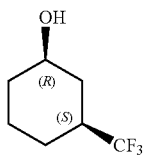

(hereinafter sometimes to be referred to as compound (6)), which are included in compound (3), is not more than 8 mol %.

[9] A method for producing a compound represented by the formula (2)

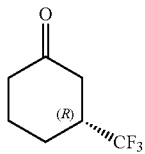

comprising bringing a carbon-carbon double bond reductase, a microorganism or cell having an ability to produce the enzyme, a processed product of the microorganism or cell, and/or a culture solution containing the enzyme which is obtained by culturing the microorganism or cell into contact with a compound represented by the formula (1)

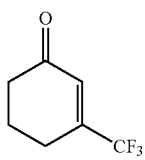 [SMILES: O=C1C=C(C(F)(F)F)CCC1]

to obtain the compound represented by the formula (2).

[10] The production method of the above-mentioned [9], wherein the aforementioned carbon-carbon double bond reductase comprises a protein shown in the following (A), (B) or (C):

(A) a protein having the amino acid sequence shown in SEQ ID NO: 1

(B) a protein having an amino acid sequence resulting from deletion, substitution, insertion and/or addition of 1 to plural amino acids in the amino acid sequence shown in SEQ ID NO: 1, and having an activity to catalyze a reaction shown in the formula (I):

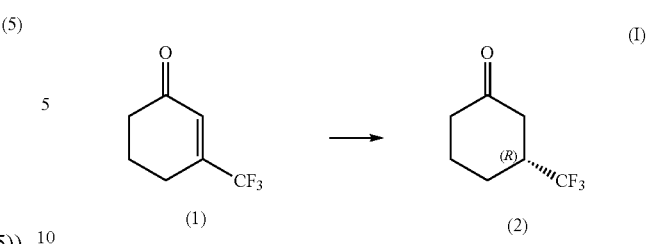

(C) a protein having an amino acid sequence with not less than 80% identity with the amino acid sequence shown in SEQ ID NO: 1, having at least one amino acid substitution selected from the following groups (i)-(ii) introduced thereinto, and having an activity to catalyze reaction(s) shown in the formula (I) and/or the formula (II)

(i) substitution of the 26th cysteine in the amino acid sequence shown in SEQ ID NO: 1 with an amino acid other than aspartic acid, phenylalanine, tryptophan and tyrosine (ii) substitution of the 104th alanine in the amino acid sequence shown in SEQ ID NO: 1 with an amino acid other than alanine.

[11] A method for producing a compound represented by the formula (4)

comprising bringing a carbonyl reductase, a microorganism or cell having an ability to produce the enzyme, a processed product of the microorganism or cell, and/or a culture solution containing the enzyme which is obtained by culturing the microorganism or cell into contact with a compound represented by the formula (1)

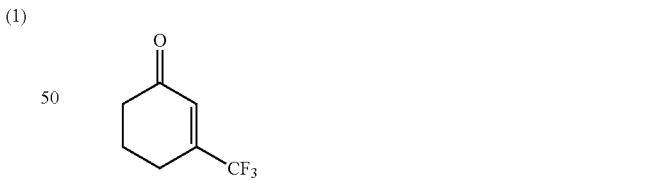

to obtain the compound represented by the formula (4).

[12] The production method of the above-mentioned [11], wherein the aforementioned carbonyl reductase comprises a protein shown in the following (A), (B) or (C):

(A) a protein having the amino acid sequence shown in SEQ ID NO: 2, 3 or 4

(B) a protein having an amino acid sequence resulting from deletion, substitution, insertion and/or addition of 1 to plural amino acids in the amino acid sequence shown in SEQ ID NO: 2, 3 or 4, and having an activity to catalyze a reaction shown in the formula (IV):

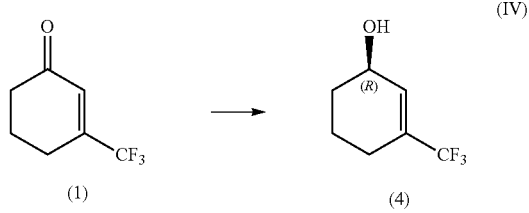

(C) a protein having an amino acid sequence with not less than 80% identity with the amino acid sequence shown in SEQ ID NO: 2, 3 or 4, and having an activity to catalyze a reaction shown in the formula (IV).

Advantageous Effects of Invention

According to the present invention, a novel method for industrially producing (1R)-3-trifluoromethyl-2-cyclohexen-1-ol or (3R)-3-(trifluoromethyl)cyclohexan-1-one useful as starting materials and intermediates for synthesizing various pharmaceutical products with high optical purity, high selectivity, and high efficiency at a low cost can be provided. Furthermore, using the thus-obtained (1R)-3-trifluoromethyl-2-cyclohexen-1-ol or (3R)-3-(trifluoromethyl)cyclohexan-1-one, (1R,3R)-3-(trifluoromethyl)cyclohexan-1-ol having high optical purity can be produced highly efficiently at a low cost.

(1R)-3-trifluoromethyl-2-cyclohexen-1-ol or (3R)-3-(trifluoromethyl)cyclohexan-1-one produced by the method of the present invention, compound (1R,3R)-3-(trifluoromethyl)cyclohexan-1-ol produced using same can be utilized as starting materials and intermediates for synthesizing various pharmaceutical products.

DESCRIPTION OF EMBODIMENTS

The present invention is explained in detail in the following.
<Production Method of the Present Invention>
In the present specification, the production methods 1-3 respectively mean the following production methods.
production method 1: production method of compound (3) including step 1 and step 2
production method 2: production method of compound (3) including step 3 and step 4
production method 3: production method of compound (3) including step 5

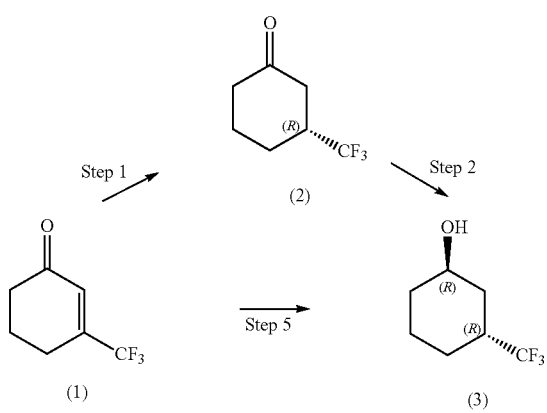

In the present specification, steps 1-5 respectively mean the following steps.
step 1: step of bringing C=C reductase and the like into contact with compound (1) to obtain compound (2)
step 2: step of bringing C=O reductase and the like into contact with compound (2) to obtain compound (3)
step 3: step of bringing C=O reductase and the like into contact with compound (1) to obtain compound (4)
step 4: step of bringing C=C reductase and the like into contact with compound (4) to obtain compound (3)
step 5: step of bringing C=C reductase and the like and C=O reductase and the like into contact with compound (1) to obtain compound (3)

The present invention is explained in detail in the following.

1. Enzyme Used in Production Method of the Present Invention [C=C Reductase]

The production method of the present invention is characterized in that a carbon-carbon double bond reductase (C=C reductase), a microorganism or cell having an ability to produce the enzyme, a processed product of the microorganism or cell, and/or a culture solution containing the enzyme which is obtained by culturing the microorganism or cell, and a carbonyl reductase (C=O reductase), a microorganism or cell having an ability to produce the enzyme, a processed product of the microorganism or cell, and/or a culture solution containing the enzyme which is obtained by culturing the microorganism or cell are brought into contact with a compound represented by the formula (1) to give a compound represented by the formula (3). In the present specification, the enzyme, a microorganism or cell having an ability to produce the enzyme, a processed product of the microorganism or cell, and/or a culture solution containing the enzyme which is obtained by culturing the microorganism or cell are sometimes to be referred to as "the enzyme and the like". The C=C reductase is explained below.

In the production method of the present invention, the C=C reductase is not particularly limited. The C=C reductase can also be obtained by, for example, purifying and isolating from Bacillus subtilis by a known method. As used herein, the purification method includes, for example, solvent extraction, distillation, column chromatography, liquid chromatography, recrystallization, combination of these, and the like.

The C=C reductase can also be produced by culturing a transformant containing a nucleic acid encoding same and separating and purifying the C=C reductase from the obtained culture. The nucleic acid encoding C=C reductase may be a DNA or RNA, or DNA/RNA chimera. Preferred is DNA. The nucleic acid may be double-stranded or single-stranded. When it is double stranded, double stranded DNA, double stranded RNA or DNA:RNA hybrid may be used. When it is single stranded, sense strand (i.e., coding strand) or antisense strand (i.e., non-coding strand) may be used.

DNA encoding C=O reductase includes, for example, the base sequence (SEQ ID NO: 5) of Bacillus subtilis-derived yqjm gene (GeneBank Accession No. P54550).

DNA encoding C═C reductase also includes synthetic DNA and the like. For example, DNA encoding *Bacillus subtilis*-derived C═C reductase can be obtained by converting full-length C═C reductase cDNA directly amplified by Reverse Transcriptase-PCR using the total RNA or mRNA fraction derived from *Bacillus subtilis* as a template, by using a known kit, for example, Mutan™-super Express Km (TAKARA BIO INC.), Mutan™-K (TAKARA BIO INC.) and the like, according to a method known per se such as ODA-LA PCR method, Gapped duplex method, Kunkel method, and the like, or a method similar thereto. Alternatively, it can also be obtained by converting, according to the above-mentioned method, cDNA cloned from the cDNA library, which is prepared by inserting the above-mentioned total RNA or mRNA fragment into an appropriate vector, by colony or plaque hybridization or PCR or the like. The vector used for the library may be any such as bacteriophage, plasmid, cosmid, phagemid and the like.

The nucleic acid (DNA) encoding C═C reductase can be cloned, for example, by PCR using a chromosomal DNA derived from *Bacillus subtilis* as a template and appropriate primers. For example, C═C reductase gene expression vector is provided by inserting a DNA encoding the C═C reductase obtained as described above into a known expression vector in a configuration permitting expression. By transforming a host cell with the expression vector, a transformant with a DNA encoding C═C reductase introduced thereinto can be obtained. The transformant can also be obtained by incorporating a DNA encoding C═C reductase into the chromosomal DNA of the host in an expressible manner by a method such as homologous recombination and the like.

In the present specification, the "expression vector" is a genetic factor used to replicate and express a protein with a desired function in a host organism by incorporating a polynucleotide that encodes the protein with the desired function in the vector and introducing the vector into the aforementioned host organism. Examples thereof include, but are not limited to, plasmid, virus, phage, cosmid and the like. Preferred expression vector is a plasmid.

In the present specification, the "transformant" means a microorganism or cell that has become capable of expressing the desired property associated with a protein having the desired function, by introducing a target gene by using the aforementioned expression vector and the like.

As a method for producing a transformant, specifically, a method including introducing a DNA encoding C═O reductase into a plasmid vector, a phage vector, or a virus vector stably present in a host cell, and introducing the constructed expression vector into the host cell, and a method including directly introducing the DNA into a host genome, and transcribing or translating the genetic information thereof can be recited as examples. In this case, it is preferable to link a suitable promoter to the 5'-side upstream of the DNA in the host, and further, it is more preferable to link the terminator to the 3'-side downstream. Such promoter and terminator are not particularly limited as long as they are promoter and terminator known to function in the cells utilized as a host and, for example, the vectors, promoters and terminators described in detail in "Microbiological Basic Lecture 8 Genetic Engineering (BISEIBUTSUGAKU KISO-KOHZA 8 IDENSHI-KOHGAKU), KYORITSU SHUPPAN CO., LTD." can be used.

The host microorganism to be the target of transformation to express C═C reductase is not particularly limited as long as the host itself does not adversely influence compound (1), compound (2), compound (4), or compound (3) and, for example, the microorganisms shown below can be mentioned.

Bacteria with established host vector system and belonging to genus *Escherichia*, genus *Bacillus*, genus *Pseudomonas*, genus *Serratia*, genus *Brevibacterium*, genus *Corynebacterium*, genus *Streptococcus*, genus *Lactobacillus*, and the like.

Actinomycetes with established host vector system and belonging to genus *Rhodococcus*, genus *Streptomyces*, and the like.

Yeast with established host vector system and belonging to genus *Saccharomyces*, genus *Kluyveromyces*, genus *Schizosaccharomyces*, genus *Zygosaccharomyces*, genus *Yarrowia*, genus *Trichosporon*, genus Rhodosporidium, genus *Hansenula*, genus *Pichia*, genus *Candida*, and the like.

Fungus with established host vector system and belonging to genus *Neurospora*, genus *Aspergillus*, genus *Cephalosporium*, genus *Trichoderma*, and the like.

The procedure for producing the transformant, the construction of the recombinant vector suitable for the host, and the method for culturing the host can be performed according to the techniques conventionally used in the fields of molecular biology, biotechnology, and genetic engineering (e.g., the method described in Molecular Cloning).

Specific examples of preferred host microorganism, preferred transformation method in each microorganism, vector, promoter, terminator and the like are given below, but the present invention is not limited to these examples.

In genus *Escherichia*, particularly *Escherichia coli*, examples of the plasmid vector include pKV32, pKW32, pBR, pUC plasmids and the like, such as promoters derived from lac (β-galactosidase), trp (tryptophan operon), tac, trc (fusion of lac, trp), A phage PL, PR and the like. Examples of the terminator include terminators derived from trpA, phage, rrnB ribosomal RNA, and the like.

In genus *Bacillus*, examples of the vector include pUB110-based plasmid, pC194-based plasmid and the like, and the vector can also be integrated with the chromosome. As the promoter and terminator, promoters and terminators of enzyme genes such as alkali protease, protease, α-amylase and the like, and the like can be used.

In genus *Pseudomonas*, examples of the vector include general host vector system established in *Pseudomonas putida, Pseudomonas cepacia* and the like, plasmids related to the decomposition of toluene compounds, wide host range vector based on TOL plasmid (including genes required for autonomous replication derived from RSF1010 and the like) pKT240 (Gene, 26, 273-82 (1983)) and the like.

In genus *Brevibacterium*, particularly *Brevibacterium lactofermentum*, examples of the vector include plasmid vectors such as pAJ43 (Gene 39, 281 (1985)) and the like. As the promoters and terminators, various promoters and terminators used for *Escherichia coli* can be used.

In genus *Corynebacterium*, particularly *Corynebacterium glutamicum*, examples of the vector include plasmid vectors such as pCS11 (JP-A-57-183799), pCB101 (Mol. Gen. Genet. 196, 175 (1984)) and the like.

In genus *Saccharomyces*, particularly *Saccharomyces cerevisiae*, examples of the vector include YRp-based, Yep-based, YCp-based, Yip-based plasmids and the like. In addition, promoters and terminators of various enzyme genes such as alcohol dehydrogenase, glyceraldehyde-3-phosphate dehydrogenase, acid phosphatase, β-galactosidase, phosphoglycerate kinase, enolase can be used.

In genus *Schizosaccharomyces*, examples of the vector include *Schizosaccharomyces pombe*-derived plasmid vector described in Mol. Cell. Biol. 6, 80 (1986), and the like. Particularly, pAUR224 is commercially available from Takara Bio Inc. and can be used easily.

In genus *Aspergillus, Aspergillus niger, Aspergillus oryzae*, and the like are most well-studied among fungus, integration with plasmid and chromosome is available, and extracellular protease and amylase-derived promoters can be used (Trendsin Biotechnology 7, 283-287 (1989)).

In addition to the above, host vector systems corresponding to various microorganisms have been established, and they can be used as appropriate.

In addition to microorganisms, various host/vector systems have been established in plant cells and animal cells. In particular, a system that expresses a large amount of heterologous protein in animal cells such as insects (for example, silkworm) and the like (Nature 315, 592-594 (1985)) and in plant cells such as rapeseed, corn, potato and the like, and a system using a cell-free protein synthesis system such as *Escherichia coli* cell-free extract, wheat germ and the like have been established and can be preferably used.

In the production method of the present invention, the "microorganism or cell having an ability to produce the enzyme" is not particularly limited as long as it is a microorganism or cell having the ability to produce "C═C reductase (activity that can stereoselectively reduce carbon-carbon double bond)", or a microorganism or cell inherently having the ability, or a microorganism or cell imparted with the ability by breeding. As a means of imparting the ability by breeding, known methods such as gene recombinant treatment (transformation), mutation treatment and the like can be adopted. Of these, a microorganism or cell transformed with a DNA encoding C═C reductase is preferable. As a transformation method, for example, methods such as introducing a C═C reductase gene, enhancing the expression of a C═C reductase gene in the biosynthetic pathway of an organic compound, reducing the expression of a C═C reductase gene in the by-product biosynthetic pathway and the like can be used. As a specific method for producing a transformant, the aforementioned explanation on the C═C reductase may be quoted.

The "microorganism or cell having an ability to produce the enzyme" in the production method of the present invention is not limited to the living microorganisms or cells, but also includes those that are dead as a living body but have enzymatic activity. It also includes the microorganisms or cells that are frozen.

The "processed product of the microorganism or cell" in the production method of the present invention means a product containing a protein having a desired function, and obtained by culturing the microorganism or cell and 1) destroying the microorganism or cell with an organic solvent (acetone, dimethyl sulfoxide (DMSO), toluene, etc.), a surfactant, or the like, 2) freeze-drying same, 3) Immobilizing same on a carrier or the like, 4) physically or enzymatically destroying same, or 5) extracting an enzyme fraction as a crude product or purified product from the treated products of the aforementioned 1)-4), or further immobilizing these on a carrier (polyacrylamide gel, carrageenan gel, etc.), or the like. The treated product may be, for example, a protein obtained by destroying the cultured microorganism or cell. The protein is obtained, for example, by using a commercially available kit (e.g., Bugbuster Master Mix (manufactured by Merck)). The treated product is hereinafter sometimes to be referred to as an "enzyme solution".

The "culture solution containing the enzyme which is obtained by culturing the microorganism or cell" in the production method of the present invention may be 1) a culture medium of the microorganism or cell (for example, when it is a suspension of the cell and a liquid medium, or when the cell is a secretory-expressing cell, a supernatant obtained by removing the cell by centrifugation or the like or a concentrate thereof), 2) a culture medium of the microorganism or cell treated with an organic solvent or the like, 3) a cell membrane of the microorganism or cell destroyed physically or enzymatically, or further, an enzyme obtained by crudely purifying or purifying 2) or 3).

Examples of the C═C reductase include one containing a protein having the amino acid sequence shown in SEQ ID NO: 1 (protein of (A)), or one containing a protein having an amino acid sequence with high identity with the amino acid sequence shown in SEQ ID NO: 1 (hereinafter sometimes to be referred to as "homologue of amino acid sequence") and having an activity of reducing compound (1) and/or compound (4) (protein of (B) or (C)) (hereinafter sometimes to be referred to as "homologue of C═C reductase") and the like. Specifically, C═C reductase includes those containing the protein of the following (A), (B) or (C).

(A) a protein having the amino acid sequence shown in SEQ ID NO: 1;

(B) a protein having an amino acid sequence resulting from deletion, substitution, insertion and/or addition of 1 to plural amino acids in the amino acid sequence shown in SEQ ID NO: 1, and having an activity to catalyze reaction(s) shown in the formula (I) and/or the formula (II):

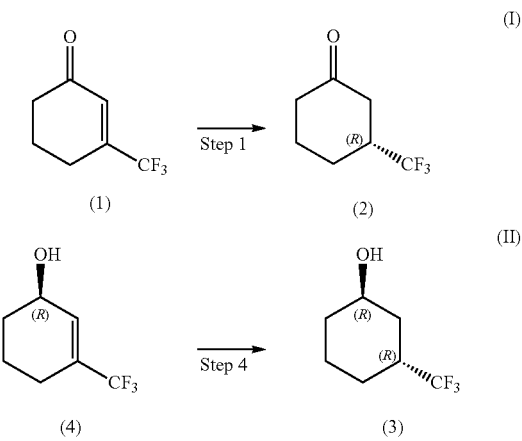

(C) a protein having an amino acid sequence with not less than 80% identity with the amino acid sequence shown in SEQ ID NO: 1, having at least one amino acid substitution selected from the following groups (i)-(ii) introduced thereinto, and having an activity to catalyze reaction(s) shown in the formula (I) and/or the formula (II):

(i) substitution of the 26th cysteine in the amino acid sequence shown in SEQ ID NO: 1 with an amino acid other than aspartic acid, phenylalanine, tryptophan and tyrosine.

(ii) substitution of the 104th alanine in the amino acid sequence shown in SEQ ID NO: 1 with an amino acid other than alanine.

In the protein of (A), the amino acid sequence shown in SEQ ID NO: 1 is the amino acid sequence of carbon-carbon double bond reductase YqjM derived from *Bacillus subtilis*.

In the present invention, the homologue of C═C reductase having the amino acid sequence shown in SEQ ID NO: 1 contains the protein of the aforementioned (B) or (C).

In the protein shown in (B), the "1 to plural amino acids" refers to generally 1-100, preferably 1-50, more preferably 1-20, further preferably 1-10, further more preferably 1-5, still more preferably 1-3, particularly preferably 1 or 2, amino acids. In the case of substitution, the amino acid is preferably substituted conservatively.

In the protein shown in (C), the amino acid substitution of the aforementioned (i) is preferably amino acid substitution of the following (i'), the amino acid substitution of the aforementioned (ii) is preferably amino acid substitution of the following (ii'), more preferably amino acid substitution of (ii''), particularly preferably amino acid substitution of (ii''').

(i') substitution of the 26th cysteine in the amino acid sequence shown in SEQ ID NO: 1 with alanine.

(ii') substitution of the 104th alanine in the amino acid sequence shown in SEQ ID NO: 1 with histidine, phenylalanine, tryptophan or tyrosine.

(ii'') substitution of the 104th alanine in the amino acid sequence shown in SEQ ID NO: 1 with histidine, tryptophan or tyrosine.

(ii''') substitution of the 104th alanine in the amino acid sequence shown in SEQ ID NO: 1 with tryptophan.

In the protein shown in (C), the amino acid substitution may be, for example, substitution of the 26th cysteine in the amino acid sequence shown in SEQ ID NO: 1 with alanine and substitution of the 104th alanine with phenylalanine, tyrosine, tryptophan or histidine (C26A and A104F, C26A and A104Y, C26A and A104W, or C26A and A104H). In addition, substitution of the 26th cysteine in the amino acid sequence shown in SEQ ID NO: 1 with alanine (C26A) can be mentioned. Furthermore, substitution of the 104th alanine in the amino acid sequence shown in SEQ ID NO: 1 with phenylalanine, tyrosine, tryptophan or histidine (A104F, A104Y, A104W, or A104H) can be mentioned. Among these amino acid substitutions, C26A and A104F, C26A and A104Y, C26A and A104W, C26A and A104H, C26A, A104F, A104Y, A104W, or A104H is preferable, C26A and A104Y, C26A and A104W, C26A and A104H, A104Y, A104W, or A104H is more preferable, and C26A and A104W, or A104W is particularly preferable.

In the protein shown in (C), the relative activity, conversion rate and optical purity with respect to the wild type can be improved by performing the above-mentioned amino acid substitutions.

In the protein shown in (C), the identity with the amino acid sequence shown in SEQ ID NO: 1 is not less than 80%, preferably not less than 85%, more preferably not less than 90%, further preferably not less than 95%, still more preferably not less than 98%, particularly preferably not less than 99%.

The identity (appropriately rephrased as homology or similarity) of the amino acid sequences in the present specification can be calculated, for example, using homology calculation algorithm NCBI BLAST (National Center for Biotechnology Information Basic Local Alignment Search Tool) and under the following conditions (expectancy=10; gap allowed; matrix=BLOSUM62; filtering=OFF). Examples of other algorithm for determining the homology of the amino acid sequence include the algorithm described in Karlin et al., Proc. Natl. Acad. Sci. USA, 90: 5873-5877 (1993) [said algorithm is incorporated in the NBLAST and XBLAST program (version 2.0) (Altschul et al., Nucleic Acids Res., 25: 3389-3402 (1997))], the algorithm described in Needleman et al., J. Mol. Biol., 48: 444-453 (1970) [said algorithm is incorporated in the GAP program in the GCG software package], the algorithm described in Myers and Miller, CABIOS, 4: 11-17 (1988) [said algorithm is incorporated in ALIGN program (version 2.0) which is a part of the CGC sequence alignment software package], the algorithm described in Pearson et al., Proc. Natl. Acad. Sci. USA, 85: 2444-2448 (1988) [said algorithm is incorporated in the FASTA program in the GCG software package] and the like, and these can also be similarly used preferably.

In the protein shown in (B) or (C), the activity to catalyze the reaction shown in the formula (I) refers to an activity to catalyze the reaction to produce compound (2) by reducing compound (1).

The selectivity in the reaction shown in the formula (I) can be confirmed by using the ratio of the (3R)-form and the (3S)-form of compound (2) produced by C=C reduction as an index. The lower the amount of the (3S)-form produced than the amount of the (3R)-form produced, the more improved is the yield of compound (2), which is advantageous in industrialization.

In the protein shown in (B) or (C), the activity to catalyze the reaction shown in the formula (II) refers to an activity to catalyze the reaction to produce compound (3) by reducing compound (4).

The selectivity in the reaction shown in the formula (II) can be confirmed by using the ratio of the (1R,3R)-form and the (1R,3S)-form of compound (3) produced by reduction as an index. The lower the amount of the (1R,3S)-form produced than the amount of the (1R,3R)-form produced, the more improved is the yield of compound (3), which is advantageous in industrialization.

The production ratio of the (1R,3R)-form and the (1R,3S)-form can be compared using the ratio of the Trans form and the Cis form produced as an index. The Trans form and Cis form mean geometric isomers, the (1R,3R)-form and the (1S,3S)-form are Trans forms, and the (1R,3S)-form and the (1S,3R)-form are Cis forms. In the present invention, since a resultant product from C=C reduction contains a (1R,3R)-form as the main component, it is possible to quantify the resultant product by using not only an evaluation system that can quantify the (1R,3R)-form alone but also an evaluation system that can separate the Trans form and the Cis form. That is, quantification of the (1R,3R)-form can be substituted by quantification of the amount of the Trans form produced. Similarly, quantification of the (1R,3S)-form can be substituted by quantification of the amount of Cis form produced. The lower the amount of the Cis form produced, the more improved is the yield of compound (3), which is advantageous in industrialization.

The selectivity of these can be confirmed by bringing compound (4) into contact with a target C=C reductase or the like to produce compound (3), and measuring the amounts produced of the (1R,3R)-form and (1R,3S)-form of compound (3), or measuring the amounts produced of the Trans form and Cis form.

A method for contact is not particularly limited. For example, compound (1) or compound (4) is added to a liquid containing the aforementioned C=C reductase to be the target, and the reaction is performed at a suitable temperature (e.g., about 10° C.-45° C.) and suitable pressure (for example, around atmospheric pressure), or the like.

As described above, C=C reductase is exemplified by one containing a protein having the amino acid sequence shown in SEQ ID NO: 1 (protein shown in (A)), or one containing a protein which is a homologue of the amino acid sequence and having the C=C reduction activity of compound (1) and/or compound (4) (protein shown in (B) or (C)) and the like. The degree of C=C reduction activity of compound (1) and/or compound (4) by C═C reductase containing the protein having the homologue of the amino acid sequence may be quantitatively equivalent to C═C reductase containing the protein having the amino acid sequence shown in SEQ ID NO: 1, but may be different within an acceptable range (e.g., about 0.1-fold to about 20-fold, preferably, about 0.3-fold to about 15-fold, further preferably about 0.5-fold to about 10-fold).

As a method for obtaining C═C reductase containing a protein shown in (A), (B) or (C), the aforementioned explanation on the method for obtaining C═C reductase, the method for producing from a transformant containing C═C reductase, or the like may be quoted.

The C═C reductase (protein shown in (B) or (C)) has an activity to catalyze the reaction(s) shown in the above-mentioned formula (I) and/or formula (II) with higher selectivity than C═C reductase containing a conventionally-known protein shown in SEQ ID NO: 1 (protein shown in (A)).

In the below-mentioned production method of the present invention, the aforementioned C═C reductase may be directly reacted with compound (1) or compound (4). It is preferable to use a microorganism or cell having an ability to produce the enzyme, a processed product of the microorganism or cell, and/or a culture solution containing the enzyme which is obtained by culturing the microorganism or cell.

[C═O Reductase]

The production method of the present invention is characterized in that a carbon-carbon double bond reductase (C═C reductase), a microorganism or cell having an ability to produce the enzyme, a processed product of the microorganism or cell, and/or a culture solution containing the enzyme which is obtained by culturing the microorganism or cell, and a carbonyl reductase (C═O reductase), a microorganism or cell having an ability to produce the enzyme, a processed product of the microorganism or cell, and/or a culture solution containing the enzyme which is obtained by culturing the microorganism or cell are brought into contact with a compound represented by the formula (1) to give a compound represented by the formula (3). The enzyme, a microorganism or cell having an ability to produce the enzyme, a processed product of the microorganism or cell, and/or a culture solution containing the enzyme which is obtained by culturing the microorganism or cell are sometimes to be referred to as "the enzyme and the like". In the following, C═O reductase is explained.

In the production method of the present invention, C═O reductase is not particularly limited. C═O reductase can also be obtained by purification and isolation from, for example, *Lactobacillus* kefir, *Pichia finlandica* or *Devosia riboflavina* according to a known method. Examples of the purification method here include solvent extraction, distillation, column chromatography, liquid chromatography, recrystallization, a combination of these and the like.

Furthermore, C═O reductase can also be produced by culturing a transformant containing a nucleic acid encoding same, and separating and purifying the C═O reductase from the resulting culture. The nucleic acid encoding C═O reductase may be DNA or RNA, or may be DNA/RNA chimera. Preferred is DNA. In addition, the nucleic acid may be double-stranded or single-stranded. When it is double stranded, it may be a double stranded DNA, a double stranded RNA or a DNA:RNA hybrid. When it is single stranded, it may be a sense strand (i.e., coding strand), or an antisense strand (i.e., non-coding strand).

As nucleic acid (DNA) encoding C═O reductase, for example, *Lactobacillus* kefir-derived lkadh gene base sequence (SEQ ID NO: 6) (GeneBank Accession No. AY267012), *Pichia finlandica*-derived pfodh1 gene base sequence (SEQ ID NO: 7) (GeneBank Accession No. AB259114.1), *Devosia riboflavina*-derived drcr1 gene base sequence (SEQ ID NO: 8) (GeneBank Accession No. BD450088.1) can be mentioned.

As DNA encoding C═O reductase, synthetic DNA and the like can be mentioned. For example, in the case of DNA encoding C═O reductase derived from *Lactobacillus* kefir, *Pichia finlandica* or *Devosia riboflavina*, it can be acquired by converting a full-length C═C reductase cDNA, which was directly amplified by Reverse Transcriptase-PCR by using total RNA or mRNA fraction derived from *Lactobacillus* kefir, *Pichia finlandica* or *Devosia riboflavina* as a template, according to a method known per se such as ODA-LA PCR method, Gapped duplex method, Kunkel method and the like, or a method analogous thereto, and by using a known kit, for example, Mutan™-super Express Km (TAKARA BIO INC.), Mutan™-K (TAKARA BIO INC.) and the like. Alternatively, it can also be acquired by converting, according to the above-mentioned method, a cDNA cloned from a cDNA library, prepared by inserting a fragment of the above-mentioned total RNA or mRNA into a suitable vector, by colony or plaque hybridization method or PCR method and the like. The vector used for the library may be any such as bacteriophage, plasmid, cosmid, phagemid and the like.

The nucleic acid (DNA) encoding C═O reductase can be cloned, for example, by performing PCR using chromosomal DNA derived from *Lactobacillus* kefir, *Pichia finlandica* or *Devosia riboflavina* as a template and appropriate primers.

For a method for producing an expression vector, a method for producing a transformant, a host microorganism to be the target of transformation, and the like, the explanation on the C═C reductase may be quoted.

In the production method of the present invention, the "microorganism or cell having an ability to produce the enzyme" is not particularly limited as long as it is a microorganism or cell having the ability to produce "C═O reductase (activity that can stereoselectively reduce carbonyl group)", or a microorganism or cell inherently having the ability, or a microorganism or cell imparted with the ability by breeding. As a means of imparting the ability by breeding, known methods such as gene recombinant treatment (transformation), mutation treatment and the like can be adopted. Of these, a microorganism or cell transformed with a DNA encoding C═O reductase is preferable. As a transformation method, for example, methods such as introducing a C═O reductase gene, enhancing the expression of a C═O reductase gene in the biosynthetic pathway of an organic compound, reducing the expression of a C═O reductase gene in the by-product biosynthetic pathway and the like can be used. As a specific method for producing a transformant, the contents described in the C═C reductase may be quoted.

For the "microorganism or cell having an ability to produce the enzyme", "processed product of the microorganism or cell" and "culture solution containing the enzyme which is obtained by culturing the microorganism or cell" in the production method of the present invention, the explanation on the C═C reductase may be quoted.

Examples of the C═O reductase include one containing a protein having the amino acid sequence shown in SEQ ID NO: 2, 3 or 4 (protein of (A)), or one containing a protein having an amino acid sequence with high identity with the amino acid sequence shown in SEQ ID NO: 1 (hereinafter sometimes to be referred to as "homologue of amino acid sequence") and having an activity of reducing compound (1) and/or compound (2) (protein of (B) or (C)) (hereinafter sometimes to be referred to as "homologue of C=O reductase") and the like. Specifically, C=O reductase includes those containing the protein of the following (A), (B) or (C).

(A) a protein having the amino acid sequence shown in SEQ ID NO: 2, 3 or 4

(B) a protein having an amino acid sequence resulting from deletion, substitution, insertion and/or addition of 1 to plural amino acids in the amino acid sequence shown in SEQ ID NO: 2, 3 or 4, and having an activity to catalyze reaction(s) shown in the formula (III) and/or the formula (IV):

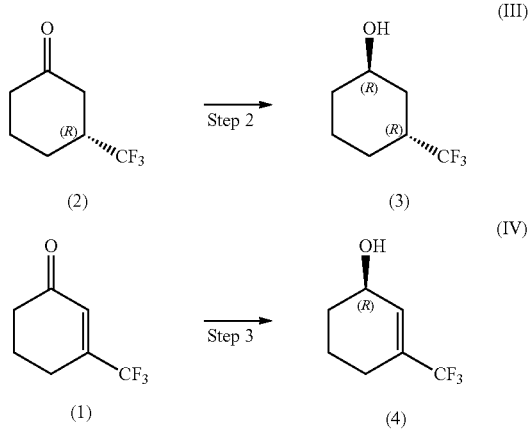

(C) a protein having an amino acid sequence having identity of not less than 80% with the amino acid sequence shown in SEQ ID NO: 2, 3 or 4, and having an activity to catalyze reaction(s) shown in the above-mentioned formula (III) and/or the formula (IV).

In the protein shown in (A), the amino acid sequence shown in SEQ ID NO: 2 is the amino acid sequence of the carbonyl reductase Lkadh derived from *Lactobacillus kefir*, and the amino acid shown in SEQ ID NO: 3 is the amino acid sequence of the carbonyl reductase PfODH derived from *Pichia finlandica*, and the amino acid sequence shown in SEQ ID NO: 4 is the amino acid sequence of the carbonyl reductase DrCR derived from *Devosia riboflavina*. These amino acid sequences have been identified by the present inventors as a C=O reductase of compound (1) or compound (2).

In the present invention, the homologue of C=O reductase having the amino acid sequence shown in SEQ ID NO: 2, 3 or 4 contains the protein of the aforementioned (B) or (C).

In the protein shown in (B), the "1 to plural amino acids" refers to generally 1-100, preferably 1-50, more preferably 1-20, further preferably 1-10, further more preferably 1-5, still more preferably 1-3, particularly preferably 1 or 2, amino acids. In the case of substitution, the amino acid is preferably substituted conservatively.

In the protein shown in (C), the identity with the amino acid sequence shown in SEQ ID NO: 2, 3 or 4 is not less than 80%, preferably not less than 85%, more preferably not less than 90%, further preferably not less than 95%, still more preferably not less than 98%, particularly preferably not less than 99%.

For the identity (may be paraphrased as homology or similarity as appropriate) of amino acid sequence, the explanation on the C=C reductase may be quoted.

In the protein shown in (B) or (C), the activity to catalyze the reaction shown in the formula (III) refers to an activity to catalyze the reaction to produce compound (3) by C=O reduction of compound (2).

In the present invention, the selectivity in the reaction shown in the formula (III) can be confirmed by using the ratio of the (1R,3R)-form and (1S,3R)-form of compound (3) produced by C=O reduction as an index. The lower the amount of the (1S,3R)-form produced than the amount of the (1R,3R)-form produced, the more improved is the yield of compound (3), which is advantageous in industrialization.

The production ratio of the (1R,3R)-form and (1S,3R)-form of compound (3) can be compared using the ratio of the Trans form and the Cis form produced as an index. The Trans form and Cis form mean geometric isomers, the (1R,3R)-form and the (1S,3S)-form are Trans forms, and the (1R,3S)-form and the (1S,3R)-form are Cis forms. In the present invention, since a resultant product from C=O reduction contains a (1R,3R)-form as the main component, it is possible to quantify the resultant product by using not only an evaluation system that can quantify the (1R,3R)-form alone but also an evaluation system that can separate the Trans form and the Cis form. That is, quantification of the (1R,3R)-form can be substituted by quantification of the amount of the Trans form produced. Similarly, quantification of the (1S,3R)-form can be substituted by quantification of the amount of Cis form produced. The lower the amount of the Cis form produced, the more improved is the yield of compound (3), which is advantageous in industrialization.

The selectivity of these can be confirmed by bringing compound (2) into contact with a target C=O reductase or the like to produce compound (3), and measuring the amounts produced of the (1R,3R)-form and (1S,3R)-form of compound (3), or measuring the amounts produced of the Trans form and Cis form.

In the protein shown in (B) or (C), the activity to catalyze the reaction shown in the formula (IV) refers to an activity to catalyze the reaction to produce compound (4) by reducing compound (1).

The selectivity in the reaction shown in the formula (IV) can be confirmed by using the ratio of the (1R)-form and the (1S)-form of compound (4) produced by reduction as an index. The lower the amount of the (1S)-form produced than the amount of the (1R)-form produced, the more improved is the yield of compound (4), which is advantageous in industrialization.

A method for contact is not particularly limited. For example, compound (1) or compound (2) is added to a liquid containing the aforementioned C=O reductase to be the target, and the reaction is performed at a suitable temperature (e.g., about 10° C.-45° C.) and suitable pressure (for example, around atmospheric pressure), or the like.

As described above, C=O reductase is exemplified by one containing a protein having the amino acid sequence shown in SEQ ID NO: 2, 3 or 4 (protein shown in (A)), or one containing a protein which is a homologue of the amino acid sequence and having the C=O reduction activity of compound (1) and/or compound (2) (protein shown in (B) or (C)) and the like. The degree of carbonyl reduction activity of compound (1) and/or compound (2) by C=O reductase containing the protein having the homologue of the amino acid sequence may be quantitatively equivalent to C=O reductase containing the protein having the amino acid sequence shown in SEQ ID NO: 2, 3 or 4, but may be different within an acceptable range (e.g., about 0.1-fold to about 20-fold, preferably, about 0.3-fold to about 15-fold, further preferably about 0.5-fold to about 10-fold).

For a method for obtaining C=O reductase containing the protein shown in (A), (B) or (C), the explanation on the C=C reductase may be quoted.

The C=O reductase (protein shown in (B) or (C)) has an activity to catalyze the reaction(s) shown in the above-mentioned formula (III) or (IV) with higher selectivity than C=O reductase containing a conventionally-known protein shown in SEQ ID NO: 2, 3 or 4 (protein shown in (A)).

In the below-mentioned production method of the present invention, the aforementioned C=O reductase may be directly reacted with compound (1) or compound (2). It is preferable to use a microorganism or cell having an ability to produce the enzyme, a processed product of the microorganism or cell, and/or a culture solution containing the enzyme which is obtained by culturing the microorganism or cell.

2. Composition of the Present Invention

The composition (enzyme) of the present invention includes C=C reductase, a microorganism or cell having an ability to produce the enzyme, a processed product of the microorganism or cell, and/or a culture solution containing the enzyme which is obtained by culturing the microorganism or cell, and catalyzes a reaction for producing compound (2) by using compound (1) as a substrate, and a reaction for producing compound (3) by using compound (4) as a substrate. The composition of the present invention is useful because it can be used as a catalyst to industrially produce compound (2) or compound (3) having high optical purity with high efficiency at a low cost.

In addition, the composition (enzyme) of the present invention includes C=O reductase, a microorganism or cell having an ability to produce the enzyme, a processed product of the microorganism or cell, and/or a culture solution containing the enzyme which is obtained by culturing the microorganism or cell, and catalyzes a reaction for producing compound (4) by using compound (1) as a substrate, and a reaction for producing compound (3) by using compound (2) as a substrate. The composition of the present invention is useful because it can be used as a catalyst to industrially produce compound (3) or compound (4) having high optical purity with high efficiency at a low cost.

The composition of the present invention may contain excipient, buffer, suspension, stabilizer, preservative, antiseptic, saline and the like, in addition to the active ingredient (enzymes, etc.). As the excipient, lactose, sorbitol, D-mannitol, sucrose and the like can be used. As the buffer, phosphate, citrate, acetate and the like can be used. As the stabilizer, propyleneglycol, ascorbic acid and the like can be used. As the preservative, phenol, benzalkonium chloride, benzyl alcohol, chlorobutanol, methylparaben and the like can be used. As the antiseptic, benzalkonium chloride, paraoxybenzoic acid, chlorobutanol and the like can be used.

3. Production Method of the Present Invention

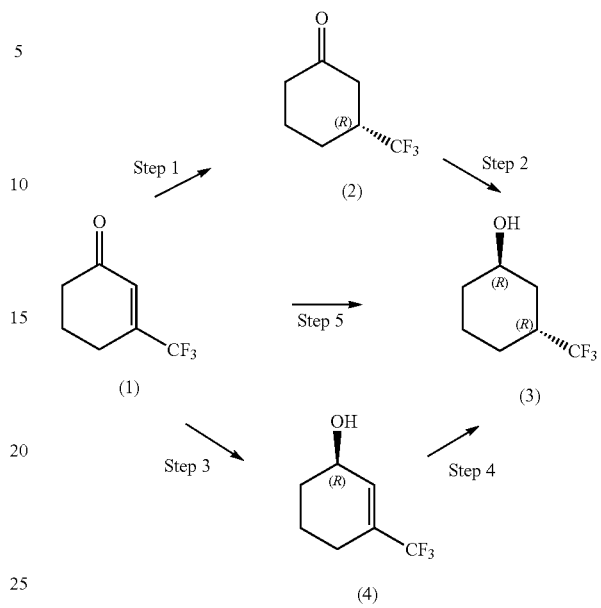

[Step 1]

Production of compound (2) by reaction shown in the following formula (I) using C=C reductase and the like According to the present invention, a method for producing compound (2) by the reaction shown in formula (I), namely, by reacting C=C reductase and the like with compound (1) is provided.

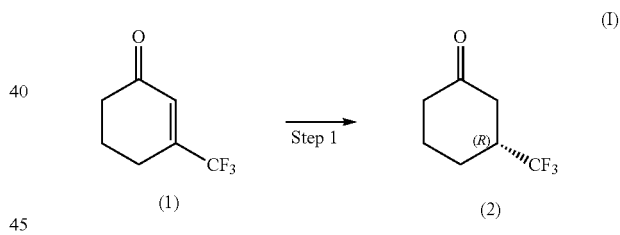

When C=C reductase is brought into contact with compound (1), purified or crudely purified C=C reductase, a microorganism or cell having an ability to produce C=C reductase (e.g., transformant having DNA encoding protein etc.), a processed product of the microorganism or cell, and/or a culture solution containing the enzyme which is obtained by culturing the microorganism or cell is brought into contact with compound (1), whereby compound (2) can be produced.

The C=C reductase may be directly used for the reaction, but it is preferable to use a microorganism or cell having an ability to produce the enzyme, a processed product of the microorganism or cell, and/or a culture solution containing the enzyme which is obtained by culturing the microorganism or cell. Among these, a transformant having a DNA encoding a protein is preferably used.

As the amount of a microorganism or cell, a processed product of the microorganism or cell, and/or a culture solution containing the enzyme which is obtained by culturing the microorganism or cell to be added to the reaction mixture, when a microorganism or cell is added, it is added to the reaction mixture such that the concentration of the microorganism or cell is generally about 0.1 w/v %-50 w/v %, preferably 1 w/v %-20 w/v %, based on the body weight of the wet bacteria. When a processed product or culture solution is used, the specific activity of the enzyme is determined, and an amount that affords the above-mentioned cell concentration upon addition is added. In the present specification, w/v % shows weight/volume %.

The method for the reaction is not particularly limited, and compound (1) to be the substrate is added to a liquid containing C═C reductase and the reaction can be performed at a suitable temperature (e.g., about 10° C.-45° C.) and a suitable pressure (for example, around atmospheric pressure). In this way, compound (2) can be produced.

Compound (1) to be the reaction substrate is generally used at a substrate concentration within the range of 0.01 w/v %-90 w/v %, preferably 0.1 w/v %-30 w/v %. The reaction substrate may be added all at once at the start of the reaction. However, it is desirable to add continuously or intermittently from the viewpoint of reducing the influence of the enzyme substrate inhibition and improving the accumulated concentration of the resultant product.

The reaction is generally performed in an aqueous medium or a mixture of an aqueous medium and an organic solvent. As the aqueous medium, for example, water or buffer can be mentioned. As the organic solvent, a solvent having high solubility of compound (1) which is a reaction substrate, such as methanol, ethanol, 1-propanol, 2-propanol, 1-butanol, tert-butanol, acetone, dimethyl sulfoxide and the like, can be used. As the organic solvent, ethyl acetate, butyl acetate, toluene, chloroform, n-hexane and the like that are effective for removing reaction by-products can also be used.

The reaction is performed at a reaction temperature of generally 4° C.-60° C., preferably 10° C.-45° C., and under the condition of generally pH3-11, preferably pH5-8. The reaction time is generally about 1 hr-72 hr.

The compound (2) produced by the production method of the present invention can be purified by separating bacteria, protein and the like in the reaction mixture by a separation or purification method known to those of ordinary skill in the art such as centrifugation, membrane treatment and the like after completion of the reaction, followed by extraction with an organic solvent such as 1-butanol, tert-butanol and the like, distillation, column chromatography using ion exchange resin, silica gel and the like, crystallization at the isoelectric point, crystallization with monohydrochloride, dihydrochloride, calcium salt, and the like, and the like in an appropriate combination.

Using compound (2) obtained in the present invention, compound (3) with high optical purity, starting materials for the synthesis, and intermediates useful for the production of intermediates for synthesis of various pharmaceutical products can be produced highly efficiently at a low cost.

[Step 2]

Production of compound (3) by reaction shown in the following formula (III) using C═O reductase and the like According to the present invention, a method for producing compound (3) by the reaction shown in formula (III), namely, by reacting C═O reductase and the like with compound (2) is provided.

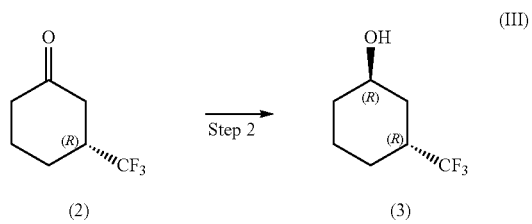

When C═O reductase is brought into contact with compound (2), purified or crudely purified C═O reductase, a microorganism or cell having an ability to produce C═O reductase of the present invention (e.g., transformant having DNA encoding protein etc.), a processed product of the microorganism or cell, and/or a culture solution containing the enzyme which is obtained by culturing the microorganism or cell is brought into contact with compound (2), whereby compound (3) can be produced.

The C═O reductase may be directly used for the reaction, but it is preferable to use a microorganism or cell having an ability to produce the enzyme, a processed product of the microorganism or cell, and/or a culture solution containing the enzyme which is obtained by culturing the microorganism or cell. Among these, a transformant having a DNA encoding a protein is preferably used.

As the amount of a microorganism or cell, a processed product of the microorganism or cell, and/or a culture solution containing the enzyme which is obtained by culturing the microorganism or cell to be added to the reaction mixture, when a microorganism or cell is added, it is added to the reaction mixture such that the concentration of the microorganism or cell is generally about 0.1 w/v %-50 w/v %, preferably 1 w/v %-20 w/v %, based on the body weight of the wet bacteria. When a processed product or culture solution is used, the specific activity of the enzyme is determined, and an amount that affords the above-mentioned cell concentration upon addition is added.

As 3-(trifluoromethyl)cyclohexan-1-one which is a reaction substrate of C═O reductase, (3R)-form is generally used.

The method for the reaction is not particularly limited, and compound (2) to be the substrate is added to a liquid containing C═O reductase and the reaction can be performed at a suitable temperature (e.g., about 10° C.-45° C.) and a suitable pressure (for example, around atmospheric pressure). In this way, compound (3) can be produced.

Compound (2) to be the reaction substrate is generally used at a substrate concentration within the range of 0.01 w/v %-90 w/v %, preferably 0.1 w/v %-30 w/v %. The reaction substrate may be added all at once at the start of the reaction. However, it is desirable to add continuously or intermittently from the viewpoint of reducing the influence of the enzyme substrate inhibition and improving the accumulated concentration of the resultant product.

The reaction is generally performed in an aqueous medium or a mixture of an aqueous medium and an organic solvent. As the aqueous medium, for example, water or buffer can be mentioned. As the organic solvent, a solvent having high solubility of compound (2) which is a reaction substrate, such as methanol, ethanol, 1-propanol, 2-propanol, 1-butanol, tert-butanol, acetone, dimethyl sulfoxide and the like, can be used. As the organic solvent, ethyl acetate, butyl acetate, toluene, chloroform, n-hexane and the like that are effective for removing reaction by-products can also be used.

The reaction is performed at a reaction temperature of generally 4° C.-60° C., preferably 10° C.-45° C., and under the condition of generally pH3-11, preferably pH5-8. The reaction time is generally about 1 hr-72 hr.

The compound (3) produced by the production method of the present invention can be purified by separating bacteria, protein and the like in the reaction mixture by a separation or purification method known to those of ordinary skill in the art such as centrifugation, membrane treatment and the like after completion of the reaction, followed by extraction with an organic solvent such as 1-butanol, tert-butanol and the like, distillation, column chromatography using ion exchange resin, silica gel and the like, crystallization at the isoelectric point, crystallization with monohydrochloride, dihydrochloride, calcium salt, and the like, and the like in an appropriate combination.

The obtained compound (3) includes a compound represented by the following formula (5)

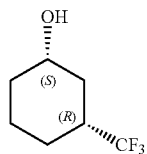

(5)

(hereinafter sometimes to be referred to as compound (5)), or a compound represented by the following formula (6)

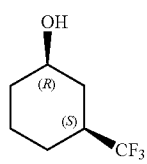

(6)

(hereinafter sometimes to be referred to as compound (6)), which is a diastereomer thereof. When compound (3) is used as a starting material or intermediate for synthesizing pharmaceutical products, these compounds are preferably used in a small content. In the compound (3) obtained by the above-mentioned production method, the content of compound (5) and/or compound (6) is preferably not more than 8 mol %, more preferably not more than 6 mol %, further preferably not more than 4 mol %, particularly preferably not more than 2 mol %.

Using compound (3) obtained in the present invention, compound with high optical purity, starting materials for the synthesis, and intermediates for synthesis of various pharmaceutical products can be produced highly efficiently at a low cost. The compound (3) obtained in the present invention can be used for the production of starting materials for synthesis and intermediates for synthesis of various pharmaceutical products without performing purification and the like since it contains a small amount of impurities. Accordingly, the production cost becomes low and compound (3) is preferable for industrial production.

[Step 3]

Production of compound (4) by reaction shown in the following formula (IV) using C=O reductase and the like According to the present invention, a method for producing compound (4) by the reaction shown in formula (IV), namely, by reacting C=O reductase and the like with compound (1) is provided.

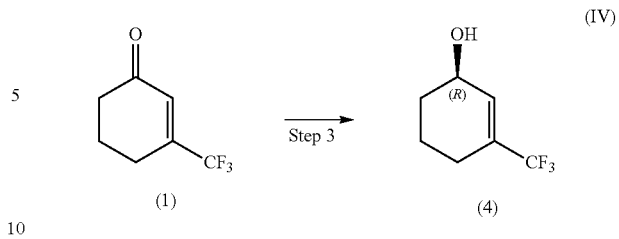

When C=O reductase is brought into contact with compound (1), purified or crudely purified C=O reductase, a microorganism or cell having an ability to produce C=O reductase (e.g., transformant having DNA encoding protein etc.), a processed product of the microorganism or cell, and/or a culture solution containing the enzyme which is obtained by culturing the microorganism or cell is brought into contact with compound (1), whereby compound (4) can be produced.

The C=O reductase may be directly used for the reaction, but it is preferable to use a microorganism or cell having an ability to produce the enzyme, a processed product of the microorganism or cell, and/or a culture solution containing the enzyme which is obtained by culturing the microorganism or cell. Among these, a transformant having a DNA encoding a protein is preferably used.

As the amount of a microorganism or cell, a processed product of the microorganism or cell, and/or a culture solution containing the enzyme which is obtained by culturing the microorganism or cell to be added to the reaction mixture, when a microorganism or cell is added, it is added to the reaction mixture such that the concentration of the microorganism or cell is generally about 0.1 w/v %-50 w/v %, preferably 1 w/v %-20 w/v %, based on the body weight of the wet bacteria. When a processed product or culture solution is used, the specific activity of the enzyme is determined, and an amount that affords the above-mentioned cell concentration upon addition is added.

As compound (1) which is a reaction substrate of C=O reductase, a commercially available product is generally used.

The method for the reaction is not particularly limited, and compound (1) to be the substrate is added to a liquid containing C=O reductase and the reaction can be performed at a suitable temperature (e.g., about 10° C.-45° C.) and a suitable pressure (for example, around atmospheric pressure). In this way, compound (4) can be produced.

Compound (1) to be the reaction substrate is generally used at a substrate concentration within the range of 0.01 w/v %-90 w/v %, preferably 0.1 w/v %-30 w/v %. The reaction substrate may be added all at once at the start of the reaction. However, it is desirable to add continuously or intermittently from the viewpoint of reducing the influence of the enzyme substrate inhibition and improving the accumulated concentration of the resultant product.

The reaction is generally performed in an aqueous medium or a mixture of an aqueous medium and an organic solvent. As the aqueous medium, for example, water or buffer can be mentioned. As the organic solvent, a solvent having high solubility of compound (1) which is a reaction substrate, such as methanol, ethanol, 1-propanol, 2-propanol, 1-butanol, tert-butanol, acetone, dimethyl sulfoxide and the like, can be used. As the organic solvent, ethyl acetate, butyl acetate, toluene, chloroform, n-hexane and the like that are effective for removing reaction by-products can also be used.

The reaction is performed at a reaction temperature of generally 4° C.-60° C., preferably 10° C.-45° C., and under the condition of generally pH3-11, preferably pH5-8. The reaction time is generally about 1 hr-72 hr.

The compound (4) produced by the production method of the present invention can be purified by separating bacteria, protein and the like in the reaction mixture by a separation or purification method known to those of ordinary skill in the art such as centrifugation, membrane treatment and the like after completion of the reaction, followed by extraction with an organic solvent such as 1-butanol, tert-butanol and the like, distillation, column chromatography using ion exchange resin, silica gel and the like, crystallization at the isoelectric point, crystallization with monohydrochloride, dihydrochloride, calcium salt, and the like, and the like in an appropriate combination.

Using compound (4) obtained in the present invention, compound (3) with high optical purity, starting materials for the synthesis of various pharmaceutical products, and intermediates useful for the production of intermediates for synthesis can be produced highly efficiently at a low cost.

[Step 4]

Production of compound (3) by reaction shown in the following formula (II) using C═C reductase and the like According to the present invention, a method for producing compound (3) by the reaction shown in formula (II), namely, by reacting C═C reductase and the like with compound (4) is provided.

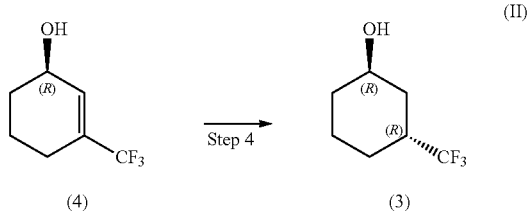

When C═C reductase is brought into contact with compound (4), purified or crudely purified C═C reductase, a microorganism or cell having an ability to produce C═C reductase (e.g., transformant having DNA encoding protein etc.) of the present invention, a processed product of the microorganism or cell, and/or a culture solution containing the enzyme which is obtained by culturing the microorganism or cell is brought into contact with compound (4), whereby compound (3) can be produced.

The C═C reductase may be directly used for the reaction, but it is preferable to use a microorganism or cell having an ability to produce the enzyme, a processed product of the microorganism or cell, and/or a culture solution containing the enzyme which is obtained by culturing the microorganism or cell. Among these, a transformant having a DNA encoding a protein is preferably used.

As the amount of a microorganism or cell, a processed product of the microorganism or cell, and/or a culture solution containing the enzyme which is obtained by culturing the microorganism or cell to be added to the reaction mixture, when a microorganism or cell is added, it is added to the reaction mixture such that the concentration of the microorganism or cell is generally about 0.1 w/v %-50 w/v %, preferably 1 w/v %-20 w/v %, based on the body weight of the wet bacteria. When a processed product or culture solution is used, the specific activity of the enzyme is determined, and an amount that affords the above-mentioned cell concentration upon addition is added.

As 3-trifluoromethyl-2-cyclohexen-1-ol which is a reaction substrate of C═C reductase, (1R)-form is generally used.

The method for the reaction is not particularly limited, and compound (4) to be the substrate is added to a liquid containing C═C reductase and the reaction can be performed at a suitable temperature (e.g., about 10° C.-45° C.) and a suitable pressure (for example, around atmospheric pressure). In this way, compound (3) can be produced.

Compound (4) to be the reaction substrate is generally used at a substrate concentration within the range of 0.01 w/v %-90 w/v %, preferably 0.1 w/v %-30 w/v %. The reaction substrate may be added all at once at the start of the reaction. However, it is desirable to add continuously or intermittently from the viewpoint of reducing the influence of the enzyme substrate inhibition and improving the accumulated concentration of the resultant product.

The reaction is generally performed in an aqueous medium or a mixture of an aqueous medium and an organic solvent. As the aqueous medium, for example, water or buffer can be mentioned. As the organic solvent, a solvent having high solubility of compound (4) which is a reaction substrate, such as methanol, ethanol, 1-propanol, 2-propanol, 1-butanol, tert-butanol, acetone, dimethyl sulfoxide and the like, can be used. As the organic solvent, ethyl acetate, butyl acetate, toluene, chloroform, n-hexane and the like that are effective for removing reaction by-products can also be used.

The reaction is performed at a reaction temperature of generally 4° C.-60° C., preferably 10° C.-45° C., and under the condition of generally pH3-11, preferably pH5-8. The reaction time is generally about 1 hr-72 hr.

The compound (3) produced by the production method of the present invention can be purified by separating bacteria, protein and the like in the reaction mixture by a separation or purification method known to those of ordinary skill in the art such as centrifugation, membrane treatment and the like after completion of the reaction, followed by extraction with an organic solvent such as 1-butanol, tert-butanol and the like, distillation, column chromatography using ion exchange resin, silica gel and the like, crystallization at the isoelectric point, crystallization with monohydrochloride, dihydrochloride, calcium salt, and the like, and the like in an appropriate combination.

The obtained compound (3) includes compound (5) or compound (6), which is a diastereomer thereof. When compound (3) is used as a starting material or intermediate for synthesizing pharmaceutical products, these compounds are preferably used in a small content. In the compound (3) obtained by the above-mentioned production method, the content of compound (5) and/or compound (6) is preferably not more than 8 mol %, more preferably not more than 6 mol %, further preferably not more than 4 mol %, particularly preferably not more than 2 mol %.

Using compound (3) obtained in the present invention, compound with high optical purity, starting materials for the synthesis, and intermediates for synthesis of various pharmaceutical products can be produced highly efficiently at a low cost. The compound (3) obtained in the present invention can be used for the production of starting materials for synthesis and intermediates for synthesis of various pharmaceutical products without performing purification and the like since it contains a small amount of impurities. Accordingly, the production cost becomes low and compound (3) is preferable for industrial production.

[Step 5]

Production of compound (3) by reaction shown in the following formula (V) using C=C reductase and the like According to the present invention, a method for producing compound (3) by the reaction shown in formula (V), namely, by reacting C=C reductase and the like with compound (1) is provided.

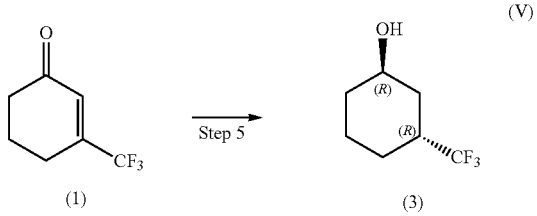

When C=C reductase and C=O reductase are brought into contact with compound (1), purified or crudely purified C=C reductase of the present invention, a microorganism or cell having an ability to produce C=C reductase (e.g., transformant having DNA encoding protein etc.), a processed product of the microorganism or cell, and/or a culture solution containing the enzyme which is obtained by culturing the microorganism or cell, and C=O reductase, a microorganism or cell having an ability to produce C=O reductase (e.g., transformant having DNA encoding protein etc.), a processed product of the microorganism or cell, and/or a culture solution containing the enzyme which is obtained by culturing the microorganism or cell are brought into contact with compound (1), whereby compound (3) can be produced.

The C=C reductase and C=O reductase may be directly used for the reaction, but it is preferable to use a microorganism or cell having an ability to produce the enzymes, a processed product of the microorganism or cell, and/or a culture solution containing the enzymes which is obtained by culturing the microorganism or cell. Among these, a transformant having a DNA encoding a protein is preferably used.

As the amount of a microorganism or cell, a processed product of the microorganism or cell, and/or a culture solution containing the enzyme which is obtained by culturing the microorganism or cell to be added to the reaction mixture, when a microorganism or cell is added, it is added to the reaction mixture such that the concentration of the microorganism or cell is generally about 0.1 w/v %-50 w/v %, preferably 1 w/v %-20 w/v %, based on the body weight of the wet bacteria. When a processed product or culture solution is used, the specific activity of the enzyme is determined, and an amount that affords the above-mentioned cell concentration upon addition is added.

The method for the reaction is not particularly limited, and compound (1) to be the substrate is added to a liquid containing C=C reductase and C=O reductase and the reaction can be performed at a suitable temperature (e.g., about 10° C.-45° C.) and a suitable pressure (for example, around atmospheric pressure). In this way, compound (3) can be produced.

Compound (1) to be the reaction substrate is generally used at a substrate concentration within the range of 0.01 w/v %-90 w/v %, preferably 0.1 w/v %-30 w/v %. The reaction substrate may be added all at once at the start of the reaction. However, it is desirable to add continuously or intermittently from the viewpoint of reducing the influence of the enzyme substrate inhibition and improving the accumulated concentration of the resultant product.

The reaction is generally performed in an aqueous medium or a mixture of an aqueous medium and an organic solvent. As the aqueous medium, for example, water or buffer can be mentioned. As the organic solvent, a solvent having high solubility of compound (1) which is a reaction substrate, such as methanol, ethanol, 1-propanol, 2-propanol, 1-butanol, tert-butanol, acetone, dimethyl sulfoxide and the like, can be used. As the organic solvent, ethyl acetate, butyl acetate, toluene, chloroform, n-hexane and the like that are effective for removing reaction by-products can also be used.

The reaction is performed at a reaction temperature of generally 4° C.-60° C., preferably 10° C.-45° C., and under the condition of generally pH3-11, preferably pH5-8. The reaction time is generally about 1 hr-72 hr.

The compound (3) produced by the production method of the present invention can be purified by separating bacteria, protein and the like in the reaction mixture by a separation or purification method known to those of ordinary skill in the art such as centrifugation, membrane treatment and the like after completion of the reaction, followed by extraction with an organic solvent such as 1-butanol, tert-butanol and the like, distillation, column chromatography using ion exchange resin, silica gel and the like, crystallization at the isoelectric point, crystallization with monohydrochloride, dihydrochloride, calcium salt, and the like, and the like in an appropriate combination.

The obtained compound (3) includes compound (5) or compound (6), which is a diastereomer thereof. When compound (3) is used as a starting material or intermediate for synthesizing pharmaceutical products, these compounds are preferably used in a small content. In the compound (3) obtained by the above-mentioned production method, the content of compound (5) and/or compound (6) is preferably not more than 8 mol %, more preferably not more than 6 mol %, further preferably not more than 4 mol %, particularly preferably not more than 2 mol %.

Using compound (3) obtained in the present invention, compound with high optical purity, starting materials for the synthesis, and intermediates for synthesis of various pharmaceutical products can be produced highly efficiently at a low cost. The compound (3) obtained in the present invention can be used for the production of starting materials for synthesis and intermediates for synthesis of various pharmaceutical products without performing purification and the like since it contains a small amount of impurities. Accordingly, the production cost becomes low and compound (3) is preferable for industrial production.

The production methods 1-3 of the present invention can be performed in the presence of a coenzyme. As the coenzyme, reduced nicotinamide adenine nucleotide (NADH), reduced nicotinamide adenine dinucleotide phosphate (NADPH), oxidized nicotinamide adenine nucleotide ($NAD^+$), or oxidized nicotinamide adenine dinucleotide phosphate ($NADP^+$) can be used, and NADPH or $NADP^+$ can be preferably used.

The amount of the coenzyme used is not particularly limited as long as it functions as a coenzyme. It is preferably added to the reaction system to a concentration of generally 0.001 mmol/L-100 mmol/L, preferably 0.01 mmol/L-10 mmol/L.

When a coenzyme is added, it is preferable to regenerate $NAD(P)^+$ generated from NAD(P)H into NAD(P)H to improve production efficiency. Examples of the regeneration method include <1> a method using the $NAD(P)^+$ reducing ability of the host microorganism itself, <2> a method of adding a microorganism having the ability to generate NAD(P)H from NAD(P)+, or a processed product thereof, or an enzyme (regenerating enzyme) that can be used for regeneration of NAD(P)H, such as glucose dehydrogenase, formate dehydrogenase, alcohol dehydrogenase, amino acid dehydrogenase, organic acid dehydrogenase (malate dehydrogenase, etc.), into the reaction system, <3> a method of introducing the gene of the above-mentioned regenerating enzyme, which is an enzyme that can be used for regeneration of NAD(P)H, simultaneously with the DNA of the present invention when producing a transformant, and the like.

Example

The present invention is described more specifically with reference to the following Examples; however, the present invention is not limited by these examples as long as it does not deviate from the gist thereof.

In the Tables shown below, A is alanine, C is cysteine, D is aspartic acid, F is phenylalanine, H is histidine, W is tryptophan, and Y is tyrosine. In addition, for example, A104W shows a mutation in which the 104th alanine in the amino acid sequence is substituted by tryptophan.

In the Examples, each abbreviation shows the following compound.
(R)-TFCH: (3R)-3-(trifluoromethyl)cyclohexan-1-one
(S)-TFCH: (3S)-3-(trifluoromethyl)cyclohexan-1-one
TFCL: 3-(trifluoromethyl)cyclohexan-1-ol
(1R,3R)-TFCL: (1R,3R)-3-(trifluoromethyl)cyclohexan-1-ol
(1S,3S)-TFCL: (1S,3S)-3-(trifluoromethyl)cyclohexan-1-ol The amount produced, purity, and the like of the target product were measured by a gas chromatography method under GC analysis condition 1 and GC analysis condition 2 shown below. The elution times of (R)-TFCH and (S)-TFCH were respectively assigned from the peaks obtained as reaction intermediates of the below-mentioned Example 1 and Reference Example 8 described later. The elution times of (1R,3R)-TFCL and (1S,3S)-TFCL are the elution times of (1R,3R)-TFCL of Example 1 and (1S,3S)-TFCL of Reference Example 8 described later, respectively. Among the four peaks detected when a mixture of 4 isomers of TFCL (TFCL isomers 1-4) is subjected to the analysis, TFCL isomer 1 is (1R,3R)-TFCL (compound (3))), TFCL isomer 2 is (1S,3S)-TFCL, and the diastereomers of these, TFCL isomer 3 or TFCL isomer 4, are two different diastereomers shown by compound (5) and compound (6).

TFCL-RPPA ester means (R)-(–)-2-phenylpropionic acid ester of TFCL.

TABLE 1

[GC analysis conditions 1]

| GC apparatus | Agilent 8890GC manufactured by Agilent |
| --- | --- |
| column | DB-35 manufactured by Agilent (0.25 mm × 30 m, 0.25 μm) |
| carrier gas | helium 1.2 mL/min |
| temperature rise program | 40° C. (2 min)→10° C./min→300° C. |
| injecting temperature | 250° C. |
| detector temperature | 300° C. |
| split ratio | 10:1 |
| injection volume | 1 μL |

TABLE 1-continued

[GC analysis conditions 1]

| elution time | (1R,3R)-TFCL-RPPA | 19.0 min |
| --- | --- | --- |
| | (1S,3S)-TFCL-RPPA | 19.1 min |
| | TFCL isomer 3-RPPA ester | 19.8 min |
| | TFCL isomer 4-RPPA ester | 19.9 min |

TABLE 2

[GC analysis conditions 2]

| GC/MS apparatus | Agilent 6890N GC manufactured by Agilent |
| --- | --- |
| column | γ-DEX225 manufactured by RESTEK (0.25 mm × 30 m, 0.25 μm) |
| carrier gas | helium 1.5 mL/min |
| temperature rise program | 85° C. (40 min)→10° C./min→180° C. (2 min) |
| injecting temperature | 250° C. |
| detector temperature | 200° C. |
| split ratio | 50:1 |
| injection volume | 1 μL |
| elution time | compound (1) 8.1 min |
| | (S)-TFCH 17.5 min |
| | (R)-TFCH 20.2 min |
| | TFCL isomer 3 21.5 min |
| | compound (4), (1S)-form 24.9 min |
| | compound (4) 24.9 min |
| | (1S,3S)-TFCL 28.2 min |
| | TFCL isomer 4 28.7 min |
| | (1R,3R)-TFCL 31.5 min |

Reference Example 1 (Preparation of Expression Plasmid)

[Preparation of Carbon-Carbon Double Bond Reductase (Hereinafter to be Referred to as "YqjM") Expression Plasmid]
(1) Gene Cloning PCR was performed according to a conventional method to obtain a DNA fragment of about 1 kbp of the yqjm gene encoding YqjM (GeneBank Accession No. P54550) derived from Bacillus subtilis. Using this DNA fragment as a template, PCR was performed according to a conventional method to obtain a DNA fragment in which a restriction enzyme cleavage site of restriction enzyme EcoRI was added to the 5' terminal and a restriction enzyme cleavage site of restriction enzyme XbaI was added to the 3' terminal.
(2) Preparation of Expression Plasmid The DNA fragment of yqjm obtained in the above-mentioned (1) was introduced into the downstream of trc promoter of a plasmid pKV32 (described in Japanese Patent No. 4270918) obtained by digesting with restriction enzymes EcoRI and XbaI, by using T4 DNA Ligase (manufactured by TAKARA BIO INC.) to give pKV32-YqjM.

Reference Example 2 (Preparation of Expression Plasmid)

[Preparation of Carbonyl Reductase (Hereinafter to be Referred to as "Lkadh") Expression Plasmid]
(1) Gene Cloning PCR was performed according to a conventional method to obtain a DNA fragment of about 0.75 kbp of the lkadh gene (GeneBank Accession No. AY267012) derived from

*Lactobacillus* kefir. Using this DNA fragment, PCR was performed according to a conventional method to obtain a DNA fragment in which a restriction enzyme cleavage site of restriction enzyme EcoRI was added to the 5' terminal and a restriction enzyme cleavage site of restriction enzyme XbaI was added to the 3' terminal.

(2) Preparation of Expression Plasmid

The DNA fragment of lkadh obtained in the above-mentioned (1) was introduced into the downstream of trc promoter of a plasmid pKV32 in the same manner as in Reference Example 1(2) to give pKV32-Lkadh.

Reference Example 3 (Preparation of Expression Plasmid)

[Preparation of Glucose Dehydrogenase (Hereinafter to be Referred to as "BsGDH") Expression Plasmid]
(1) Gene Cloning According to the method described in JP-B-6476110, a DNA fragment of about 0.8 kbp of the gene sequence bsgdh gene encoding *Bacillus subtilis*-derived BsGDH (GenBank Accession No. NP_388275) protein in which the 96th amino acid is substituted by alanine and the 252nd amino acid is substituted by leucine was obtained. Using this DNA fragment, PCR was performed according to a conventional method to obtain a DNA fragment in which a restriction enzyme cleavage site of restriction enzyme EcoRI was added to the 5' terminal and a restriction enzyme cleavage site of restriction enzyme XbaI was added to the 3' terminal.

(2) Preparation of Expression Plasmid

Using T4 DNA Ligase (manufactured by TAKARA BIO INC.), the DNA fragment of bsgdh obtained in the above-mentioned (1) was introduced into the downstream of trc promoter of plasmid pKW32 (described in JP-B-5613660) digested with restriction enzymes EcoRI and XbaI to give pKW32-BsGDH.

Reference Example 4 (Preparation of Expression Plasmid)

Using the plasmid pKV32-YqjM obtained in Reference Example 1 as a template, a mutation-introduced plasmid having the amino acid sequence shown in SEQ ID NO: 1 in which the 26th amino acid C was replaced with any of A, D, F, W, Y, and the 104th amino acid A was replaced with any of F, H, W, Y was produced. The mutation-introduced plasmids produced are shown in Table 3.

TABLE 3

| name | mutation-introduced residue and mutation | |
| --- | --- | --- |
| YqjM WT (wild-type) | C26 | A104 |
| YqjM variant 1 | W | F |
| YqjM variant 2 | W | Y |
| YqjM variant 3 | W | W |
| YqjM variant 4 | W | H |
| YqjM variant 5 | W | A |
| YqjM variant 6 | A | F |
| YqjM variant 7 | A | Y |
| YqjM variant 8 | A | W |
| YqjM variant 9 | A | H |
| YqjM variant 10 | A | A |
| YqjM variant 11 | C | F |
| YqjM variant 12 | C | Y |
| YqjM variant 13 | C | W |
| YqjM variant 14 | C | H |
| YqjM variant 15 | D | W |
| YqjM variant 16 | F | W |
| YqjM variant 17 | Y | W |

Reference Example 5 (Preparation of Expression Plasmid)

[Preparation of Carbon-Carbon Double Bond Reductase (Hereinafter to be Referred to as "NEMA") Expression Plasmid]
(1) Gene Cloning PCR was performed according to a conventional method to obtain a DNA fragment of about 1 kbp of the nemA gene encoding *Escherichia coli*-derived NEMA (described in Biol. Pharm. Bull. 20:110-112 (1997)). Using this DNA fragment as a template, PCR was performed according to a conventional method to obtain a DNA fragment in which a restriction enzyme cleavage site of restriction enzyme EcoRI was added to the 5' terminal and a restriction enzyme cleavage site of restriction enzyme XbaI was added to the 3' terminal.

(2) Preparation of Expression Plasmid

The DNA fragment of nemA obtained in the above-mentioned (1) was introduced into the downstream of trc promoter of a plasmid pKV32 in the same manner as in Reference Example 1(2) to give pKV32-NEMA.

Reference Example 6 (Preparation of Expression Plasmid)

[Preparation of Carbonyl Reductase (Hereinafter to be Referred to as "IsADH") Expression Plasmid]
(1) Gene Cloning PCR was performed according to a conventional method to obtain a DNA fragment of about 1 kbp of the isadh gene (described in JP-B-4205496) derived from *Issatchankia scutulata* var. *scutulata* JCM1828 strain. Using this DNA fragment, PCR was performed according to a conventional method to obtain a DNA fragment in which a restriction enzyme cleavage site of restriction enzyme EcoRI was added to the 5' terminal and a restriction enzyme cleavage site of restriction enzyme XbaI was added to the 3' terminal.

(2) Preparation of Expression Plasmid

The DNA fragment of isadh obtained in the above-mentioned (1) was introduced into the downstream of trc promoter of a plasmid pKV32 in the same manner as in Reference Example 1(2) to give pKV32-IsADH.

Reference Example 7 (Preparation of Bacterial Cell)

[Preparation of *Escherichia coli* JM109 Expressing Various Enzymes]
(1) Preparation of Expression Strain Using the plasmids obtained in Reference Examples 1-6, *Escherichia coli* JM109 competent cell (manufactured by TAKARA BIO INC.) was transformed according to a conventional method to obtain recombinant *Escherichia coli* with the plasmid introduced thereinto.

(2) Preparation of Enzyme Solution

The recombinant *Escherichia coli* obtained in the above-mentioned (1) was grown in LB medium containing kanamycin (25 µg/mL), 0.2 mmol/L isopropyl β-D-thiogalactopyranoside (IPTG) at 30° C. for 18 hr. After collecting 2 mL of the obtained bacterial cell broth by centrifugation, an enzyme solution was obtained according to a conventional method and using Bugbuster Master Mix (manufactured by Merck) added with Benzonase and rLysozyme.

Example 1: Preparation of TFCL (TFCL Isomer 1) (Compound (3))

(1) Preparation of TFCL Isomer 1

7 mL of 1 mol/L potassium phosphate buffer (pH7.0), 5.6 mL of 50 mmol/L $NADP^+$, 10.5 mL of 1 mol/L glucose solution, 718 mg of compound (1), an enzyme solution of *Escherichia coli* JM109/pKV32-YqjM (A104W(YqjM variant 13)) obtained in Reference Examples 4 and 7, an enzyme solution of *Escherichia coli* JM109/pKV32-Lkadh obtained in Reference Examples 2 and 7, and an enzyme solution of *Escherichia coli* JM109/pKW32-BsGDH (E96A, Q252L) obtained in Reference Examples 3 and 7 were mixed in a 200 mL jar fermentor, and pure water was added to prepare 70 mL of a reaction mixture. The reaction mixture was reacted overnight at a reaction temperature of 28° C.-30° C. at pH7.0 during reaction under a sufficient stirring speed.

After completion of the reaction, methyl tert-butyl ether (hereinafter to be referred to as MTBE) was added to the reaction mixture, the mixture was stirred at room temperature, and the MTBE layer was obtained. MTBE was evaporated from the extract using a rotary evaporator to give TFCL isomer 1.

(2) Preparation of TFCL Isomer 1-RPPA Ester by Modified Moscher Method

In a 30 mL test tube were charged (R)-(−)-2-phenylpropionic acid (RPPA) (15 mg, 0.1 mmol), N,N-dimethylaminopyridine (1.2 mg, 0.01 mmol) and TFCL isomer 1 (20.2 mg, 0.12 mmol) obtained in the above-mentioned (1), dichloromethane solvent (200 μL) was added, and the mixture was reacted by stirring at room temperature. The reaction mixture was analyzed by GC analysis conditions 1 and production of the target substance was confirmed. The obtained reaction mixture was cooled to 0° C., N,N'-dicyclohexylcarbodiimide (24.7 mg, 0.12 mmol) was added, and the mixture was reacted at room temperature for 3 hr. After the reaction, water (200 μL) was added for partitioning, and the organic layer was recovered. The organic layer was filtered, and the obtained filtrate was concentrated under reduced pressure in a rotary evaporator. The concentrated residue was purified by silica gel column to give the desired TFCL isomer 1-RPPA ester as an oily substance.

TFCL Isomer 1-RPPA Ester

GC-MS (CI:$CH_4$ gas): m/z=301 (M+H) rational formula $C_{16}H_{19}F_3O_2$ Calculated 300.1337

$^1$H-NMR ($CDCl_3$, 400 MHz):

TABLE 4

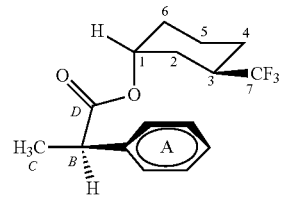

| chemical shift (ppm) | multiplicity (J value) | hydrogen number | assignment |
|---|---|---|---|
| 7.4-7.2 | m | 5 | A |
| 5.2 | br | 1 | 1 eq |

TABLE 4-continued

| chemical shift (ppm) | multiplicity (J value) | hydrogen number | assignment |
|---|---|---|---|
| 3.8 | q (7.2 Hz) | 1 | B |
| 2.0-1.9 | m | 1 | 2 eq |
| 1.9-1.8 | m | 2 | 6 eq |
|  |  |  | 4 eq |
| 1.8 | m | 1 | 3 ax |
| 1.7-1.6 | m | 1 | 5 eq |
| 1.5 | d (7.2 Hz) | 3 | C |
| 1.5-1.4 | m | 3 | 5 ax |
|  |  |  | 6 ax |
|  |  |  | 2 ax |
| 1.3-1.2 | m | 1 | 4 ax | eq: equatorial
ax: axial

Reference Example 8: Preparation of TFCL (TFCL Isomer 2)

(1) Preparation of TFCL Isomer 2

The reaction was performed in the same manner as in Example 1 except that an enzyme solution of *Escherichia coli* JM109/pKV32-YqjM was changed to an enzyme solution of *Escherichia coli* JM109/pKV32-NEMA obtained in Reference Examples 5 and 7, and an enzyme solution of *Escherichia coli* JM109/pKV32-Lkadh was changed to an enzyme solution of *Escherichia coli* JM109/pKV32-IsADH obtained in Reference Examples 6 and 7.

After completion of the reaction, MTBE was added to the reaction mixture, the mixture was stirred at room temperature, and the MTBE layer (extract) was obtained. MTBE was evaporated from the extract using a rotary evaporator to give TFCL isomer 2.

(2) Preparation of TFCL Isomer 2-RPPA Ester by Modified Moscher Method

In a 30 mL test tube were charged (R)-(−)-2-phenylpropionic acid (RPPA) (15 mg, 0.1 mmol), N,N-dimethylaminopyridine (1.2 mg, 0.01 mmol) and TFCL isomer 2 (20.2 mg, 0.12 mmol) obtained in the above-mentioned (1), dichloromethane solvent (200 μL) was added, and the mixture was reacted by stirring at room temperature. The reaction mixture was analyzed by GC analysis conditions 1 and production of the target substance was confirmed. The obtained reaction mixture was cooled to 0° C., N,N'-dicyclohexylcarbodiimide (24.7 mg, 0.12 mmol) was added, and the mixture was reacted at room temperature for 3 hr. After the reaction, water (200 μL) was added for partitioning, and the organic layer was recovered. The organic layer was filtered, and the obtained filtrate was concentrated under reduced pressure in a rotary evaporator. The concentrated residue was purified by silica gel column to give the desired TFCL isomer 2-RPPA ester as an oily substance.

TFCL Isomer 2-RPPA Ester

GC-MS(CI:$CH_4$ gas): m/z=301 (M+H), rational formula C16H19F3O2 Calculated 300.1337

$^1$H-NMR ($CDCl_3$, 400 MHz):

TABLE 5

| chemical shift (ppm) | multiplicity (J value) | hydrogen number | assignment |
|---|---|---|---|
| 7.4-7.2 | m | 5 | A |
| 5.2 | d (2.7 Hz) | 1 | 1 eq |
| 3.8 | q (7.2 Hz) | 1 | B |
| 2.3-2.2 | m | 1 | 3 ax |
| 2.2-2.1 | m | 1 | 2 eq |
| 1.9-1.7 | m | 2 | 4 eq 6 eq |
| 1.6 | d (7.2 Hz) | 3 | C |
| 1.6-1.5 | m | 1 | 5 eq 2 ax |
| 1.4-1.3 | m | 1 | 6 aq |
| 1.3-1.2 | m | 2 | 4 ax 5 ax | eq: equatorial
ax: axial

From the analysis data of $^1$H-NMR and GC-MS of the TFCL isomer 1-RPPA ester obtained in Example 1 (2) and the TFCL isomer 2-RPPA ester obtained in Reference Example 8 (2), the following structure was supported.

TABLE 6

| | Example 1 | Reference Example 8 |
|---|---|---|
| compound | TFCL isomer 1-RPPA ester | TFCL isomer 2-RPPA ester |
| structural formula | | |
| steric configuration | (1R, 3R) | (1S, 3S) |

From the $^1$H-NMR of the TFCL isomer 1-RPPA ester obtained in Example 1 (2) and the TFCL isomer 2-RPPA ester obtained in Reference Example 8 (2), it was determined that the 1-position hydrogen is in the equatorial position since the J value of the 1-position proton is 2.7 Hz or broad and the value is small.

In general, the improved Mocsher method can determine the steric configuration by confirming a phenomenon in which protons close to the benzene ring shift to a high magnetic field.

Comparing the chemical shifts of the 3-position proton, it was confirmed that the TFCL isomer 1-RPPA ester shifted to a higher magnetic field of 0.4 ppm to 0.5 ppm than the TFCL isomer 2-RPPA ester, and the benzene ring of the TFCL isomer 1-RPPA ester is closer to the 3-position proton (TFCL isomer 1-RPPA ester: 1.8 ppm, TFCL isomer 2-RPPA ester: 2.2 ppm-2.3 ppm).

From the above, it was determined that the TFCL isomer 1 obtained in Example 1 (1) is a (1R,3R)-form, and the TFCL isomer 2 obtained in Reference Example 8 (1) is a (1S,3S)-form.

Examples 2-11 and Comparative Examples 1-8: Measurement of Initial Activity of YqjM Variant The measurement activity of the initial activity of YqjM variant was confirmed by measuring the amount of decrease in NADPH when compound (1) was added at a wavelength of 340 nm. 10 μL of enzyme solution (Example 2: enzyme solutions obtained in Reference Examples 1 and 7 were used, Examples 3-11 and Comparative Examples 1-8: enzyme solutions obtained in Reference Examples 4 and 7 were used), 25 μL of 1 mol/L potassium phosphate buffer (pH7), 10 μL of 8 mmol/L NADPH, 200 μL of water, and 5 μL of DMSO solution of compound (1) (0.1 mol/L) were mixed. The mixture was placed in a 96-well plate (manufactured by Corning), and the change in absorbance at 340 nm was measured for 2 min using a microplate reader (manufactured by Molecular Bio) warmed to 30° C. The average value (mOD/min) of the absorbance change per unit time was calculated, and the activity value per unit time/unit protein was calculated from the slope of the absorbance change by the following formula. The molar absorption coefficient of NADPH was calculated as 6.3 mL/μmol·cm.

activity value (μmol/min/mg-protein)=(-1)×slope of absorbance change×250 μL/10 μL/6300/0.55/protein concentration The relative activity of each variant with respect to the wild type is shown in Table 7. The case where the relative activity is less than 15% is shown with "-".

TABLE 7

| name | | mutation-introduced residue and mutation | | relative activity [%] to wild-type |
|---|---|---|---|---|
| Example 2 | YqjM wild-type | C26 | A104 | 100 |
| Comparative Example 1 | YqjM variant 1 | W | F | — |
| Comparative Example 2 | YqjM variant 2 | W | Y | — |
| Comparative Example 3 | YqjM variant 3 | W | W | — |
| Comparative Example 4 | YqjM variant 4 | W | H | — |
| Comparative Example 5 | YqjM variant 5 | W | A | — |
| Example 3 | YqjM variant 6 | A | F | 511 |
| Example 4 | YqjM variant 7 | A | Y | 544 |
| Example 5 | YqjM variant 8 | A | W | 774 |
| Example 6 | YqjM variant 9 | A | H | 640 |
| Example 7 | YqjM variant 10 | A | A | 228 |
| Example 8 | YqjM variant 11 | C | F | 410 |
| Example 9 | YqjM variant 12 | C | Y | 600 |
| Example 10 | YqjM variant 13 | C | W | 918 |
| Example 11 | YqjM variant 14 | C | H | 707 |
| Comparative Example 6 | YqjM variant 15 | D | W | — |
| Comparative Example 7 | YqjM variant 16 | F | W | — |
| Comparative Example 8 | YqjM variant 17 | Y | W | — |

As is clear from Table 2, it was found that substitution of the 26th C with A (Example 7: YqjM variant 10) or substitution of the 104th A with F, Y, W or H (Examples 8-11: YqjM variants 11-14) showed markedly improved relative activity to the wild-type. In addition, it was found that substitution of the 26th C with A along with substitution of the 104th A with F, Y, W or H (Examples 3-6: YqjM variants 6-9) also showed markedly improved relative activity to the wild-type.

On the other hand, it was found that substitution of the 26th C with W, D, F or Y (Comparative Examples 1-5: YqjM variants 1-5, Comparative Examples 6-8: YqjM variants 15-17) showed markedly decreased relative activity to the wild-type. Particularly, it was found that the reactivity to the compounds described in non-patent document 2 and the reactivity to compound (1) of the present invention are greatly different in C26W/A104F (Comparative Example 1: YqjM variant 1), C26W/A104Y (Comparative Example 2: YqjM variant 2), and C26D/A104W (Comparative Example 6: YqjM variant 15).

Examples 12-21: Production of (R)-TFCH (Compound (2))

An enzyme solution of pKV32-YqjM-introduced recombinant *Escherichia coli* prepared by the methods of Reference Examples 1 and 7 or an enzyme solution of pKV32-YqjM-introduced recombinant *Escherichia coli* prepared by the methods of Reference Examples 4 and 7 (100 µL), 50 g/L KRED mix N (manufactured by Codexis) (400 µL), and compound (1) (4.1 mg) were added to a 2 mL microtube, and the mixture was reacted by stirring at 30° C. for 1 hr. To the obtained reaction mixture was added heptane (1 mL) and the mixture was stirred at room temperature. The upper layer obtained after standing was analyzed under GC analysis condition 2. The conversion rate from compound (1) to TFCH and the optical purity of the obtained (R)-TFCH (compound (2)) are shown in Table 8. The conversion rate and optical purity were calculated by the following formulas.

$$\text{conversion rate } [\%] = \frac{C2(R) + C2(S)}{C1 + C2(R) + C2(S)} \times 100 \quad \text{[formula 1]}$$

$$\text{optical purity } [\%ee] = \frac{|C2(R) - C2(S)|}{C2(R) + C2(S)} \times 100$$

C1: compound (1) concentration [mmol/L]
C2(R): (R)-TFCH concentration [mmol/L]
C2(S): (S)-TFCH concentration [mmol/L]

TABLE 8

| Example | mutation-name | introduced residue and mutation | | (R)-TFCH conversion rate [%] | optical purity [% ee] |
|---|---|---|---|---|---|
| Example 12 | YqjM wild-type | 026 | A104 | 46.6 | 80.0 |
| Example 13 | YqjM variant 6 | A | F | 65.3 | 93.7 |
| Example 14 | YqjM variant 7 | A | Y | 64.2 | 93.6 |
| Example 15 | YqjM variant 8 | A | W | 70.2 | 94.8 |
| Example 16 | YqjM variant 9 | A | H | 65.3 | 93.7 |
| Example 17 | YqjM variant 10 | A | A | 49.9 | 87.6 |
| Example 18 | YqjM variant 11 | C | F | 65.2 | 94.2 |
| Example 19 | YqjM variant 12 | C | Y | 74.0 | 95.8 |
| Example 20 | YqjM variant 13 | C | W | 78.1 | 96.1 |
| Example 21 | YqjM variant 14 | C | H | 72.9 | 95.4 |

As is clear from Table 8, it was found that YqjM variants 6-10 (Examples 13-17) with substitution of the 26th C with A showed markedly improved conversion rate and optical purity compared with the wild-type. Furthermore, it was found that YqjM variants 6-9 (Examples 13-16) with substitution of the 104th A with F, Y, W or H showed further improved conversion rate and optical purity.

Example 22: Production of (1R,3R)-TFCL (Compound (3))

7 mL of 1 mol/L potassium phosphate buffer (pH7.0), 0.7 mL of 50 mmol/L NADP$^+$, 10.5 mL of 4 mol/L glucose solution, 33 mL of pure water, 2873 mg of compound (1), 8.4 mL of the enzyme solution equivalent to the wet bacteria (0.84 g) of *Escherichia coli* JM109/pKV32-YqjM (A104W (YqjM variant 13)) obtained in Reference Examples 4 and 7, 4.2 mL of the enzyme solution equivalent to the wet bacteria (0.42 g) of *Escherichia coli* JM109/pKV32-Lkadh obtained in Reference Examples 2 and 7, and 6.1 mL of the enzyme solution equivalent to the wet bacteria (0.61 g) of *Escherichia coli* JM109/pKW32-BsGDH (E96A, Q252L) obtained in Reference Examples 3 and 7 were mixed in a 200 mL jar fermentor, and the mixture was reacted for 17 hr under a sufficient stirring speed at a reaction temperature of 28° C.-30° C. and using 25 wt % NaOH water-solubility while keeping pH 7.0 during the reaction.

After completion of the reaction, 35 mL of methyl tert-butyl ether (hereinafter to be referred to as MTBE) was added to the reaction mixture, the mixture was stirred at room temperature, and the MTBE layer containing (1R,3R)-TFCL was obtained. MTBE (35 mL) was added again to the obtained aqueous layer, the mixture was stirred at room temperature, and the MTBE layer containing (1R,3R)-TFCL was obtained. As a result of the purity analysis and optical purity analysis of the obtained MTBE layer under GC analysis conditions 2, the pure content of (1R,3R)-TFCL was 2348 mg, and the yield was 81.8%. The optical purity was 99.8% e.e. The diastereomer was 1.6%. The optical purity and existence ratio of diastereomer were calculated by the following formulas.

$$\text{optical purity } [\%ee] = \frac{|C3(RR) - C3(SS)|}{C3(RR) + C3(SS)} \times 100 \quad \text{[formula 2]}$$

diastereomer existence ratio [%] =

$$\frac{C3(RS) + C3(SR)}{C3(RR) + C3(SS) + C3(RS) + C3(SR)} \times 100$$

C3 (RR): (1R,3R)-TFCL concentration [mmol/L]
C3 (SS): (1S,3S)-TFCL concentration [mmol/L]
C3 (RS): (1R,3S)-TFCL concentration [mmol/L]
C3 (SR): (1S,3R)-TFCL concentration [mmol/L]

Example 23: Production of (1R,3R)-TFCL (Compound (3))

(1) Production of (R)-TFCH (Compound (2))

50 µL of 1 mol/L potassium phosphate buffer (pH7.0), 20 µL of 50 mmol/L NAD$^+$, 20 µL of 50 mmol/L NADP$^+$, 75 µL of 1 mol/L glucose solution, 8.2 mg of compound (1), an enzyme solution of *Escherichia coli* JM109/pKV32-YqjM obtained in Reference Examples 1 and 7, and an enzyme solution of *Escherichia coli* JM109/pKW32-BsGDH (E96A, Q252L) obtained in Reference Examples 3 and 7 were mixed in a 2 mL microtube, pure water was added to prepare 500 µL of reaction mixture A. In the same manner as in reaction mixture A, reaction mixture B was prepared for analysis, and reaction mixtures A and B were reacted at reaction temperature 30° C. for 16 hr under a sufficient stirring speed.

After the reaction, heptane (1 mL) was added to reaction mixture B and the mixture was stirred at room temperature for 1 min. The upper layer obtained after standing was analyzed under GC analysis condition 2. The conversion rate from compound (1) to compound (2) was 43.1%, and the optical purity of the obtained compound (2) was 67.8% ee. The conversion rate and optical purity were calculated by the following formulas.

$$\text{conversion rate } [\%] = \frac{C2(R) + C2(S)}{C1 + C2(R) + C2(S)} \times 100 \quad \text{[formula 3]}$$

$$\text{optical purity } [\%ee] = \frac{|C2(R) - C2(S)|}{C2(R) + C2(S)} \times 100$$

C1: compound (1) concentration [mmol/L]
C2(R): (R)-TFCH concentration [mmol/L]
C2(S): (S)-TFCH concentration [mmol/L]

(2) Production of (1R,3R)-TFCL (Compound (3))

The reaction mixture A obtained in the above-mentioned (1) was further reacted for 8 hr at reaction temperature 30° C. under a sufficient stirring speed. To the reaction mixture A were added 20 µL of 50 mmol/L NAD$^+$, 20 µL of 50 mmol/L NADP$^+$, 75 µL of 1 mol/L glucose solution, and 100 µL of an enzyme solution of *Escherichia coli* JM109/pKV32-Lkadh obtained in Reference Examples 2 and 7, and the mixture was further reacted for 16 hr. To the obtained reaction mixture was added heptane (1 mL), and the mixture was stirred at room temperature for 1 min. The upper layer obtained after standing was analyzed under GC analysis condition 2. The optical purity of the obtained (1R,3R)-TFCL (compound (3)) was 75.8% ee. The diastereomer existence ratio was 23.8%. The optical purity and diastereomer existence ratio were calculated by the following formulas.

$$\text{optical purity } [\%ee] = \frac{|C3(RR) - C3(SS)|}{C3(RR) + C3(SS)} \times 100 \quad \text{[formula 4]}$$

diastereomer existence ratio [%] =

$$\frac{C3(RS) + C3(SR)}{C3(RR) + C3(SS) + C3(RS) + C3(SR)} \times 100$$

C3 (RR): (1R,3R)-TFCL concentration [mmol/L]
C3 (SS): (1S,3S)-TFCL concentration [mmol/L]
C3 (RS): (1R,3S)-TFCL concentration [mmol/L]
C3 (SR): (1S,3R)-TFCL concentration [mmol/L]

Example 24: Production of (1R)-3-trifluoromethyl-2-cyclohexen-1-ol (Compound (4))

50 µL of 1 mol/L potassium phosphate buffer (pH 7.0), 20 µL of 50 mmol/L NAD$^+$, 20 µL of 50 mmol/L NADP$^+$, 75 µL of 1 mol/L glucose solution, 8.2 mg of compound (1), an enzyme solution of *Escherichia coli* JM109/pKV32-Lkadh obtained in Reference Examples 2 and 7, and an enzyme solution of *Escherichia coli* JM109/pKW32-BsGDH (E96A, Q252L) obtained in Reference Examples 3 and 7 were mixed in a 2 mL microtube, and pure water was added to prepare 500 µL of a reaction mixture. The mixture was reacted for 23 hr at a reaction temperature of 30° C. under a sufficient stirring speed. Heptane (1 mL) was added to the obtained reaction mixture, and the mixture was stirred at room temperature for 1 min. The upper layer obtained after standing was subjected to GC-MS analysis and the production of (1R)-3-trifluoromethyl-2-cyclohexen-1-ol (compound (4)) was confirmed. The resultant product was assumed to be (1R)-form from the results of Examples 1, 22 and 23(2). The conversion rate from compound (1) to compound (4) was 43.6%. The conversion rate was calculated from the following formula.

$$\text{conversion rate } [\%] = \frac{C4(R) + C4(S)}{C1 + C4(R) + C4(S)} \times 100 \quad \text{[formula 5]}$$

C1: compound (1) concentration [mmol/L]
C4(R): compound (4) concentration [mmol/L]
C4(S): compound (4) (1S)-form concentration [mmol/L]

INDUSTRIAL APPLICABILITY

According to the present invention, a novel method for industrially producing (1R)-3-trifluoromethyl-2-cyclohexen-1-ol or (3R)-3-(trifluoromethyl)cyclohexan-1-one useful as starting materials and intermediates for synthesizing various pharmaceutical products with high optical purity, high selectivity, and high efficiency at a low cost can be provided. Furthermore, using the thus-obtained (1R)-3-trifluoromethyl-2-cyclohexen-1-ol or (3R)-3-(trifluoromethyl)cyclohexan-1-one, (1R,3R)-3-(trifluoromethyl)cyclohexan-1-ol having high optical purity can be produced highly efficiently at a low cost.

The invention claimed is:

1. A method for producing a compound represented by the formula (3):

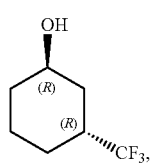

comprising:

bringing a carbon-carbon double bond reductase enzyme, a microorganism or cell having an ability to produce the carbon-carbon double bond reductase enzyme, a processed product of the microorganism or cell, and/or a culture solution containing the carbon-carbon double bond reductase enzyme which is obtained by culturing the microorganism or cell, and a carbonyl reductase enzyme, a microorganism or cell having an ability to produce the carbonyl reductase enzyme, a processed product of the microorganism or cell, and/or a culture solution containing the carbonyl reductase enzyme which is obtained by culturing the microorganism or cell into contact with a compound represented by the formula (1):

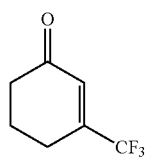
(1)

to obtain the compound represented by the formula (3); wherein:
the carbon-carbon double bond reductase enzyme comprises a protein shown in the following (A), (B), or (C):
(A) a protein having the amino acid sequence shown in SEQ ID NO: 1;
(B) a protein having an amino acid sequence resulting from deletion, substitution, insertion, and/or addition of 1 to 50 amino acids in the amino acid sequence shown in SEQ ID NO: 1, and having an activity to catalyze reaction(s) shown in the formula (I) and/or the formula (II):

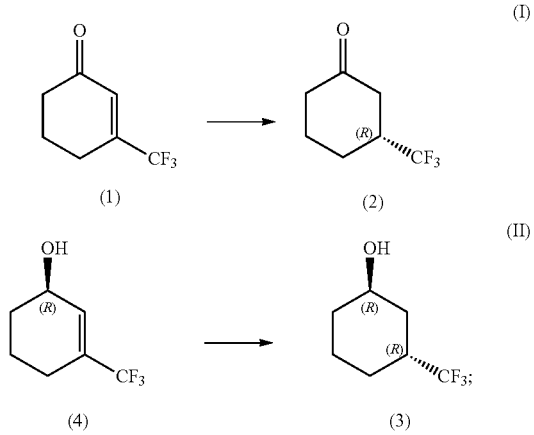

(C) a protein having an amino acid sequence with not less than 85% identity with the amino acid sequence shown in SEQ ID NO: 1, having at least one amino acid substitution selected from the following groups (i) and (ii) introduced thereinto, and having an activity to catalyze reaction(s) shown in the formula (I) and/or the formula (II):
(i) substitution of the 26$^{th}$ cysteine in the amino acid sequence shown in SEQ ID NO: 1 with an amino acid other than aspartic acid, phenylalanine, tryptophan, and tyrosine,
(ii) substitution of the 104$^{th}$ alanine in the amino acid sequence shown in SEQ ID NO: 1 with an amino acid other than alanine; and
the carbonyl reductase enzyme comprises a protein shown in the following (D), (E), or (F):
(D) a protein having the amino acid sequence shown in SEQ ID NOS: 2, 3, or 4;
(E) a protein having an amino acid sequence resulting from deletion, substitution, insertion, and/or addition of 1 to 50 amino acids in the amino acid sequence shown in SEQ ID NOS: 2, 3, or 4, and having an activity to catalyze reaction(s) shown in the formula (III) and/or the formula (IV):

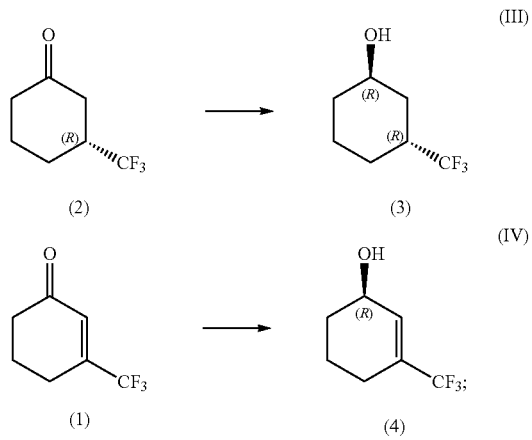

(F) a protein having an amino acid sequence with not less than 85% identity with the amino acid sequence shown in SEQ ID NOS: 2, 3, or 4, and having an activity to catalyze reaction(s) shown in the formula (III) and/or the formula (IV).

2. The production method according to claim 1, wherein the amino acid substitution in (i) is the following (i'):
(i') substitution of the 26$^{th}$ cysteine in the amino acid sequence shown in SEQ ID NO: 1 with alanine.

3. The production method according to claim 1, wherein the amino acid substitution in (ii) is the following (ii'):
(ii') substitution of the 104$^{th}$ alanine in the amino acid sequence shown in SEQ ID NO: 1 with histidine, phenylalanine, tryptophan, or tyrosine.

4. The production method according to claim 1, wherein the carbon-carbon double bond reductase enzyme, the microorganism or cell having an ability to produce the carbon-carbon double bond reductase enzyme, the processed product of the microorganism or cell, and/or the culture solution containing the carbon-carbon double bond reductase enzyme which is obtained by culturing the microorganism or cell is brought into contact with the compound represented by the formula (1):

to obtain a compound represented by the formula (2):

and further the carbonyl reductase enzyme, the microorganism or cell having an ability to produce the carbonyl reductase enzyme, the processed product of the microorganism or cell, and/or the culture solution containing the carbonyl reductase enzyme which is obtained by culturing the microorganism or cell is brought into contact with the compound represented by the formula (2) to obtain the compound represented by the formula (3):

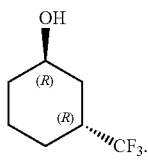
(3)

5. The production method according to claim 1, wherein the carbonyl reductase enzyme, a microorganism or cell having an ability to produce the carbonyl reductase enzyme, a processed product of the microorganism or cell, and/or a culture solution containing the carbonyl reductase enzyme which is obtained by culturing the microorganism or cell is brought into contact with the compound represented by the formula (1):

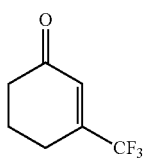
(1)

to obtain a compound represented by the formula (4):

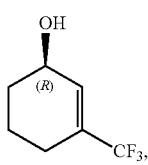
(4)

and further carbon-carbon double bond reductase enzyme, a microorganism or cell having an ability to produce the carbon-carbon double bond reductase enzyme, a processed product of the microorganism or cell, and/or a culture solution containing the carbon-carbon double bond reductase enzyme which is obtained by culturing the microorganism or cell is brought into contact with the compound represented by the formula (4) to obtain the compound represented by the formula (3):

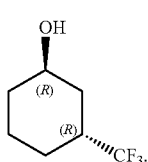
(3)

6. The production method according to claim 1, wherein a content of a compound represented by the formula (5):

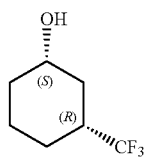
(5)

and/or a compound represented by the formula (6):

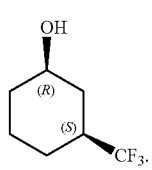
(6)

which are included in compound (3), is not more than 8 mol %.

7. A method for producing a compound represented by the formula (2):

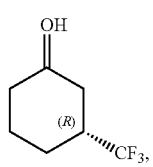
(2)

comprising bringing a carbon-carbon double bond reductase enzyme, a microorganism or cell having an ability to produce the carbon-carbon double bond reductase enzyme, a processed product of the microorganism or cell, and/or a culture solution containing the carbon-carbon double bond reductase enzyme which is obtained by culturing the microorganism or cell into contact with a compound represented by the formula (1):

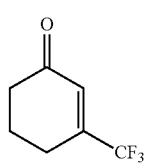
(1)

to obtain the compound represented by the formula (2); wherein:
the carbon-carbon double bond reductase enzyme comprises a protein shown in the following (A), (B), or (C):
(A) a protein having the amino acid sequence shown in SEQ ID NO: 1;
(B) a protein having an amino acid sequence resulting from deletion, substitution, insertion, and/or addition of 1 to 50 amino acids in the amino acid sequence shown in SEQ ID NO: 1, and having an activity to catalyze reaction(s) shown in the formula (I) and/or the formula (II):

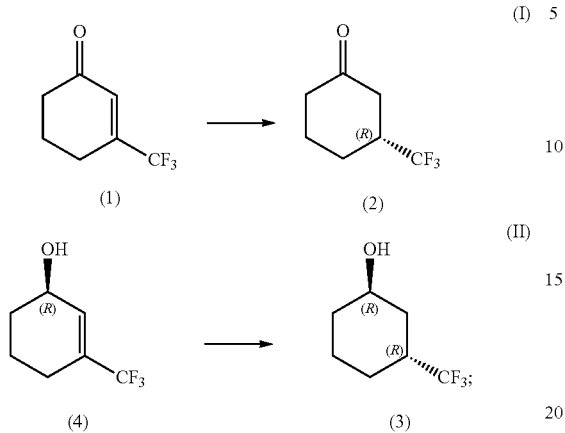

(C) a protein having an amino acid sequence with not less than 85% identity with the amino acid sequence shown in SEQ ID NO: 1, having at least one amino acid substitution selected from the following groups (i) and (ii) introduced thereinto, and having an activity to catalyze reaction(s) shown in the formula (I) and/or the formula (II):
(i) substitution of the 26$^{th}$ cysteine in the amino acid sequence shown in SEQ ID NO: 1 with an amino acid other than aspartic acid, phenylalanine, tryptophan, and tyrosine,
(ii) substitution of the 104$^{th}$ alanine in the amino acid sequence shown in SEQ ID NO: 1 with an amino acid other than alanine.

8. A method for producing a compound represented by the formula (4):

comprising bringing a carbonyl reductase enzyme, a microorganism or cell having an ability to produce the carbonyl reductase enzyme, a processed product of the microorganism or cell, and/or a culture solution containing the carbonyl reductase enzyme which is obtained by culturing the microorganism or cell into contact with a compound represented by the formula (1):

to obtain the compound represented by the formula (4); wherein the carbonyl reductase enzyme comprises a protein shown in the following (A), (B), or (C):
(A) a protein having the amino acid sequence shown in SEQ ID NOS: 2, 3, or 4;
(B) a protein having an amino acid sequence resulting from deletion, substitution, insertion, and/or addition of 1 to 50 amino acids in the amino acid sequence shown in SEQ ID NOS: 2, 3, or 4, and having an activity to catalyze reaction(s) shown in the formula (III) and/or the formula (IV):

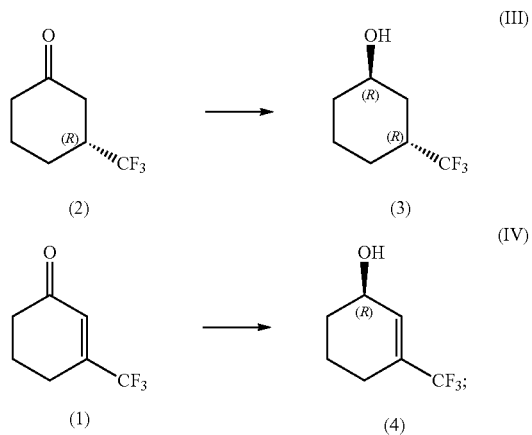

(C) a protein having an amino acid sequence with not less than 85% identity with the amino acid sequence shown in SEQ ID NOS: 2, 3, or 4, and having an activity to catalyze reaction(s) shown in the formula (III) and/or the formula (IV).

* * * * *